United States Patent
Yodfat et al.

(10) Patent No.: US 8,480,649 B2
(45) Date of Patent: Jul. 9, 2013

(54) METHOD FOR SELECTING BOLUS DOSES AND BOLUS DELIVERY PATTERNS IN A DRUG DELIVERY DEVICE

(76) Inventors: Ofer Yodfat, Modi'in (IL); Gali Shapira, Haifa (IL); Iddo Gescheit, Tel Aviv (IL)

( * ) Notice: Subject to any disclaimer, the term of this patent is extended or adjusted under 35 U.S.C. 154(b) by 236 days.

(21) Appl. No.: 12/990,179

(22) PCT Filed: Apr. 28, 2009

(86) PCT No.: PCT/IL2009/000454
§ 371 (c)(1),
(2), (4) Date: Jan. 7, 2011

(87) PCT Pub. No.: WO2009/133558
PCT Pub. Date: Nov. 5, 2009

(65) Prior Publication Data
US 2011/0106050 A1 May 5, 2011

Related U.S. Application Data

(60) Provisional application No. 61/048,856, filed on Apr. 29, 2008.

(51) Int. Cl.
*A61M 31/00* (2006.01)
*G05B 15/00* (2006.01)
*G05D 11/00* (2006.01)
*G06F 7/00* (2006.01)

(52) U.S. Cl.
USPC ............... 604/504; 604/66; 700/87; 700/282; 707/758

(58) Field of Classification Search
USPC .................. 604/65–67, 30–34, 218, 131, 154, 604/504; 700/87, 282; 707/758
See application file for complete search history.

(56) References Cited

U.S. PATENT DOCUMENTS

| | | | |
|---|---|---|---|
| 5,681,285 | A | 10/1997 | Ford et al. |
| 6,852,104 | B2 | 2/2005 | Blomquist |
| 6,936,029 | B2 | 8/2005 | Mann et al. |
| 7,291,107 | B2 | 11/2007 | Hellwig et al. |
| 2005/0065760 | A1 | 3/2005 | Murtfeldt et al. |
| 2007/0106218 | A1 | 5/2007 | Yodfat et al. |
| 2007/0191702 | A1 | 8/2007 | Yodfat et al. |
| 2008/0214916 | A1 | 9/2008 | Yodfat et al. |
| 2008/0215035 | A1 | 9/2008 | Yodfat et al. |
| 2008/0234663 | A1 | 9/2008 | Yodfat et al. |
| 2010/0256593 | A1 | 10/2010 | Yodfat et al. |

FOREIGN PATENT DOCUMENTS

| | | |
|---|---|---|
| WO | WO 2007/000425 A2 | 1/2007 |
| WO | WO 2007/093981 A2 | 8/2007 |
| WO | WO 2008/078318 A2 | 7/2008 |
| WO | WO 2008/078319 A1 | 7/2008 |
| WO | WO 2008/114254 A1 | 9/2008 |
| WO | WO 2009/066288 A1 | 5/2009 |

(Continued)

OTHER PUBLICATIONS

DCCT Trial, N. Engl J. Med 1993; 329: 977-986.

(Continued)

*Primary Examiner* — Kevin C Sirmons
*Assistant Examiner* — William Carpenter
(74) *Attorney, Agent, or Firm* — Mintz Levin Cohn Ferris Glovsky and Popeo, P.C.

(57) ABSTRACT

Embodiments of the present disclosure include methods, systems and devices for selecting a bolus configuration and may include one or more of providing a user interface for selection of one or more user interface elements, where each element corresponds to a bolus configuration of a drug, each element is spatially positioned within a multi-dimensional space corresponding to at least three dimensions and the element's position corresponding to each dimension.

19 Claims, 25 Drawing Sheets

FOREIGN PATENT DOCUMENTS

WO    WO 2009/125398 A2    10/2009

OTHER PUBLICATIONS

UKPDS Trial, Lancet 1998; 352: 837-853.
BMJ 1998; 317, (7160): 703-13.
EDIC Trial, N Engl J Med 2005; 353, (25): 2643-53.
http://www.diabetesnet.com/diabetes_tools/glycemic_index.php, Oct. 28, 2010.
J. Walsh R. Roberts, C.B. Varma and T. Bailey, "Using Insulin, Everything You Need for Success with Insulin" *Torrey Pines Press*, 2003.

| Total daily insulin dose (TDD) [IU/day] | 2200 Rule [mg\dL] | 2000 Rule [mg\dL] | 1800 Rule [mg\dL] | 1600 Rule [mg\dL] |
|---|---|---|---|---|
| 20 | 110 | 100 | 90 | 80 |
| 25 | 88 | 80 | 72 | 64 |
| 30 | 73 | 67 | 60 | 53 |
| 35 | 63 | 57 | 51 | 46 |
| 40 | 55 | 50 | 45 | 40 |
| 50 | 44 | 40 | 36 | 32 |
| 60 | 37 | 33 | 30 | 27 |
| 75 | 29 | 27 | 24 | 21 |
| 100 | 22 | 20 | 18 | 16 |

FIG. 1

Insulin sensitivity table grid, point drop per unit of insulin

| Total daily insulin dose (TDD) [IU/day] | 500 Rule [gram] | 450 Rule [gram] |
|---|---|---|
| 20 | 25 | 23 |
| 25 | 20 | 18 |
| 30 | 17 | 15 |
| 35 | 14 | 13 |
| 40 | 13 | 11 |
| 50 | 10 | 9 |
| 60 | 8 | 8 |

FIG. 2

Carb to insulin ratio, carbs covered by 1 unit of insulin

| Dose Given [IU] | Units left to work after: | | | | |
|---|---|---|---|---|---|
| | 1 Hr | 2 Hr | 3 Hr | 4 Hr | 5 Hr |
| 1 | 0.8 | 0.6 | 0.4 | 0.2 | 0 |
| 2 | 1.6 | 1.2 | 0.8 | 0.4 | 0 |
| 3 | 2.4 | 1.8 | 1.2 | 0.6 | 0 |
| 4 | 3.2 | 2.4 | 1.6 | 0.8 | 0 |
| 5 | 4.0 | 3.0 | 2.0 | 1.0 | 0 |
| 6 | 4.8 | 3.6 | 2.4 | 1.2 | 0 |
| 7 | 5.6 | 4.2 | 2.8 | 1.4 | 0 |
| 8 | 6.4 | 4.8 | 3.2 | 1.6 | 0 |
| 9 | 7.2 | 5.4 | 3.6 | 1.8 | 0 |
| 10 | 8.0 | 6.0 | 4.0 | 2.0 | 0 |

*FIG. 3*

Insulin residue, insulin units left to work

| Cereals | | Snacks | | Pasta | | Beans | |
|---|---|---|---|---|---|---|---|
| All Bran | 51 | chocolate bar | 49 | cheese tortellini | 50 | Baked | 44 |
| Bran Buds + psyll | 45 | corn chips | 72 | fettucini | 32 | black beans, boiled | 30 |
| Bran Flakes | 74 | croissant | 67 | linguini | 50 | butter, boiled | 33 |
| Cheerios | 74 | doughnut | 76 | macaroni | 46 | cannellini beans | 31 |
| Corn Chex | 83 | graham crakers | 74 | spagh, 5 min boiled | 33 | garbanzo, boiled | 34 |
| Cornflakes | 83 | jelly beans | 80 | spagh, 15 min boiled | 44 | kidney, boiled | 29 |
| Cream of Wheat | 66 | Life Savers | 70 | spagh, prot enrich | 28 | kidney, canned | 52 |
| Frosted Flakes | 55 | oatmeal cookie | 57 | vermicelli | 35 | lentils, green, brown | 30 |
| Grapenuts | 67 | pizza, cheese & tom | 60 | Soups/Vegetables | | lima, boiled | 32 |
| Life | 66 | Pizza Hut, supreme | 33 | beets, canned | 64 | navy beans | 38 |
| muesli, natural | 54 | popcorn, light micro | 55 | black bean soup | 64 | pinto, boiled | 39 |
| Nutri-grain | 66 | potato chips | 56 | carrots, fresh, boil | 49 | red lentils, boiled | 27 |
| oatmeal, old fash | 48 | pound cake | 54 | corn, sweet | 56 | soy, boiled | 16 |
| Puffed Wheat | 67 | Power bars | 58 | french fries | 75 | Breads | |
| Raisin Bran | 73 | pretzels | 83 | grean pea, soup | 66 | bagel, plain | 72 |
| Rice Chex | 89 | saltine crakers | 74 | green pea, frozen | 47 | baquette, Frnch | 95 |
| Shredded Wheat | 67 | shortbread cookies | 64 | lima beans, frozen | 32 | Croissant | 67 |

*FIG. 4*

| Special K | 54 | Snickers bar | 41 | parsnips | 97 | dark rey | 76 |
|---|---|---|---|---|---|---|---|
| Total | 76 | strawberry jam | 51 | peas, fresh, boil | 48 | Hamburger bun | 61 |
| Fruit | | vanilla wafers | 77 | pot, new, boiled | 59 | Muffins | |
| apple | 38 | Wheat Thins | 67 | pot, red, baked | 93 | apple, cin | 44 |
| apricots | 57 | Crackers | | pot, sweet | 52 | Blueberry | 59 |
| banana | 56 | graham | 74 | pot, white, boiled | 63 | oat & raisin | 54 |
| cantalope | 65 | rice cakes | 80 | pot, white, mashed | 70 | Pita | 57 |
| cherries | 22 | rye | 68 | split pea soup w/ham | 66 | pizza, cheese | 60 |
| dates | 103 | soda | 72 | tomato soup | 38 | pumpernickel | 49 |
| grapefruit | 25 | Wheat Thins | 67 | yam | 54 | Sourdough | 54 |
| grapes | 46 | Cereal Grains | | Milk Products | | Rye | 64 |
| kiwi | 52 | barley | 25 | chocolate milk | 35 | White | 70 |
| mango | 55 | basmati white rice | 58 | custard | 43 | Wheat | 68 |
| orange | 43 | bulgar | 48 | ice cream, van | 60 | Drinks | |
| papaya | 58 | couscous | 65 | ice milk, van | 50 | apple juice | 40 |
| peach | 42 | cornmeal | 68 | skim milk | 32 | colas | 65 |
| pear | 58 | millet | 71 | soy milk | 31 | Gatorade | 78 |
| pineapple | 66 | | | tofu frozen dessert | 115 | grapefruit juice | 48 |
| plums | 39 | fructose | 22 | whole milk | 30 | orange juice | 46 |
| prunes | 15 | honey | 62 | yogurt, fruit | 36 | pineapple juice | 46 |
| raisins | 64 | maltose | 105 | yogurt, plain | 14 | | |
| watermelon | 72 | table sugar | 64 | | | | |

FIG. 4 (Cont.)

| | Small Carb load | Medium Carb Load | Large Carb Load |
|---|---|---|---|
| High BG | | | |
| High GI | 5U Immediate Bolus | 7U Immediate Bolus | 9U Immediate Bolus |
| Intermediate GI | 5U 2h extended Bolus | 7U 2h extended Bolus | 9U 2h extended Bolus |
| Low GI | 5U 6h extended Bolus | 7U 6h extended Bolus | 9U 6h extended Bolus |

| CIR = 30g/u<br>IS = 80mg/dL/Unit<br>Selected GI - low<br>Delivery pattern –<br>extended bolus 6 hours | Meal containing small amounts of carbohydrate (<30g) | Meal containing medium amounts of carbohydrate (30:g<60) | Meal containing large amounts of carbohydrate (60:g<100) | Meal containing very large amounts of carbohydrate (100:g) |
|---|---|---|---|---|
| Current BG < 100mg/dL | 0U | 0.3U | 1.5U | 2.6U |
| 100mg/dL <Current BG<200mg/dL | 1.2U | 2.1U | 3.3U | 4.4U |
| 200mg/dL <Current BG<300 mg/dL | 3.7U | 4.6U | 5.7U | 6.9U |
| 300mg/dL< Current BG | 5.7U | 6.6U | 7.8U | 8.9U |

FIG. 11a

| CIR = 15g/u<br>IS = 40mg/dL/Unit<br>Selected GI - low<br>Delivery pattern –<br>extended bolus 6 hours | Meal containing small amounts of carbohydrate (<30g) | Meal containing medium amounts of carbohydrate (30:g<60) | Meal containing large amounts of carbohydrate (60:g<100) | Meal containing very large amounts of carbohydrate (100:g) |
|---|---|---|---|---|
| Current BG < 100mg/dL | 0U | 1.7U | 3.7U | 6.3U |
| 100mg/dL < Current BG < 200mg/dL | 1.7U | 3.4U | 5.8U | 8.1U |
| 200mg/dL< Current BG < 300 mg/dL | 4.2U | 5.92U | 8.2U | 10.5U |
| 300mg/dL< Current BG | 6.3U | 7.9U | 10.3U | 12.6U |

| CIR = 7.5g/u<br>IS = 20mg/dL/Unit<br>Selected GI - low<br>Delivery pattern –<br>extended bolus 6 hours | Meal containing small amounts of carbohydrate (<30g) | Meal containing medium amounts of carbohydrate (30:g<60) | Meal containing large amounts of carbohydrate (60:g<100) | Meal containing very large amounts of carbohydrate (100:g) |
|---|---|---|---|---|
| Current BG < 100mg/dL | 0U | 3.3U | 8U | 12.7U |
| 100mg/dL<Current BG<200mg/dL | 3.5U | 6.8U | 11.5U | 16.2U |
| 200mg/dL<Current BG<300 mg/dL | 8.4U | 11.8U | 16.5U | 21.1U |
| 300mg/dL< Current BG | 12.5U | 15.9U | 20.5U | 25.2U |

FIG. 11d

| CIR = 15g/u<br>IS = 40mg/dL/Unit<br>Selected GI - low<br>Delivery pattern –<br>extended bolus 8 hours | Meal containing small amounts of carbohydrate (<30g) | Meal containing medium amounts of carbohydrate (30:g<60) | Meal containing large amounts of carbohydrate (60:g<100) | Meal containing very large amounts of carbohydrate (100:g) |
|---|---|---|---|---|
| Current BG < 100mg/dL | 0U | 1.7U | 3.7U | 6.3U |
| 100mg/dL < Current BG <200mg/dL | 1.7U | 3.4U | 5.8U | 8.1U |
| 200mg/dL< Current BG < 300 mg/dL | 4.2U | 5.92U | 8.2U | 10.5U |
| 300mg/dL< Current BG | 6.3U | 7.9U | 10.3U | 12.6U |

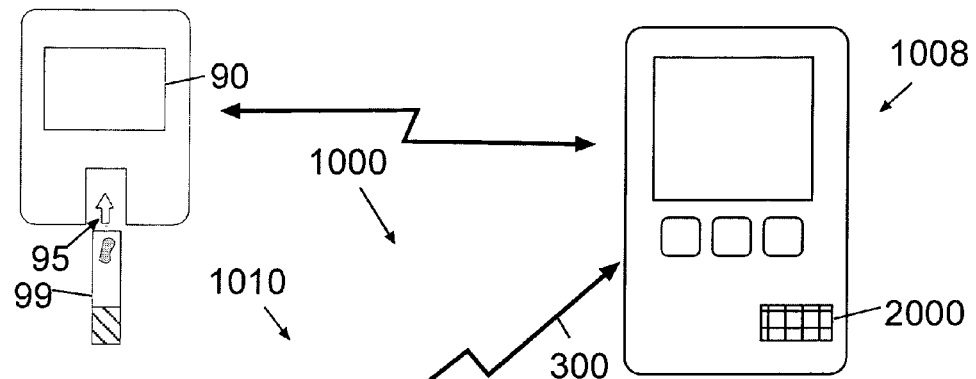
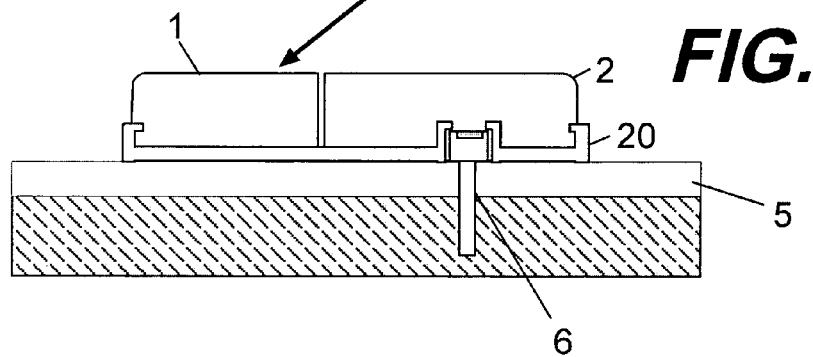
FIG. 16c
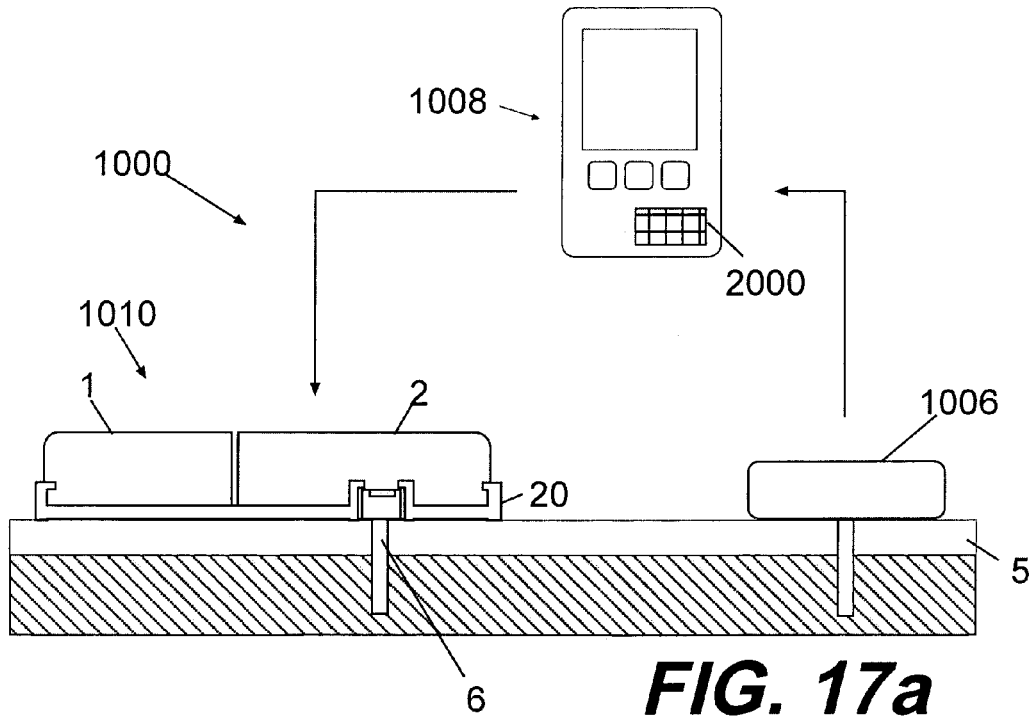
FIG. 17a

| IS | 40 | | | CARBS | | | | | |
|---|---|---|---|---|---|---|---|---|---|
| | | | Low | 10 | 20 | 40 | 60 | 80 | 100 |
| Target BG | 100 | | High | 20 | 40 | 60 | 80 | 100 | 120 |
| | BG | | Ref. | 10 | 25 | 45 | 65 | 85 | 105 |
| Low | High | Ref. | | | | | | | |
| 40 | 70 | 55 | | 0.00 | 0.75 | 2.25 | 3.75 | 5.25 | 6.75 |
| 70 | 100 | 85 | | 0.38 | 1.50 | 3.00 | 4.50 | 6.00 | 7.50 |
| 100 | 130 | 115 | | 1.13 | 2.25 | 3.75 | 5.25 | 6.75 | 8.25 |
| 130 | 160 | 145 | | 1.88 | 3 | 4.50 | 6.00 | 7.50 | 9.00 |
| 160 | 190 | 175 | | 2.63 | 3.75 | 5.25 | 6.75 | 8.25 | 9.75 |
| 190 | 220 | 205 | | 3.38 | 4.50 | 6.00 | 7.50 | 9.00 | 10.50 |
| 220 | 250 | 235 | | 4.13 | 5.25 | 6.75 | 8.25 | 9.75 | 11.25 |
| 250 | 280 | 265 | | 4.88 | 6.00 | 7.50 | 9.00 | 10.50 | 12.00 |
| 280 | 310 | 295 | | 5.63 | 6.75 | 8.25 | 9.75 | 11.25 | 12.75 |
| 310 | 340 | 325 | | 6.38 | 7.50 | 9.00 | 10.50 | 12.00 | 13.50 |
| 340 | 370 | 355 | | 7.13 | 8.25 | 9.75 | 11.25 | 12.75 | 14.25 |
| 370 | 400 | 385 | | 7.88 | 9.00 | 10.50 | 12.00 | 13.50 | 15.00 |

FIG. 20a

| | | | | CARBS | | | | | |
|---|---|---|---|---|---|---|---|---|---|
| | | | Low | 10 | 20 | 40 | 60 | 80 | 100 |
| | | | High | 20 | 40 | 60 | 80 | 100 | 120 |
| | BG | | Ref. | 10 | 25 | 45 | 65 | 85 | 105 |
| Low | High | Ref. | | Minimal Undershoot | | | | | |
| 40 | 70 | 55 | | 70 | 70 | 70 | 70 | 70 | 70 |
| 70 | 100 | 85 | | 85 | 70 | 70 | 70 | 70 | 70 |
| 100 | 130 | 115 | | 85 | 70 | 70 | 70 | 70 | 70 |
| 130 | 160 | 145 | | 85 | 70 | 70 | 70 | 70 | 70 |
| 160 | 190 | 175 | | 85 | 70 | 70 | 70 | 70 | 70 |
| 190 | 220 | 205 | | 85 | 70 | 70 | 70 | 70 | 70 |
| 220 | 250 | 235 | | 85 | 70 | 70 | 70 | 70 | 70 |
| 250 | 280 | 265 | | 85 | 70 | 70 | 70 | 70 | 70 |
| 280 | 310 | 295 | | 85 | 70 | 70 | 70 | 70 | 70 |
| 310 | 340 | 325 | | 85 | 70 | 70 | 70 | 70 | 70 |
| 340 | 370 | 355 | | 85 | 70 | 70 | 70 | 70 | 70 |
| 370 | 400 | 385 | | 85 | 70 | 70 | 70 | 70 | 70 |

FIG. 20b

| | | | CARBS | | | | | |
|---|---|---|---|---|---|---|---|---|
| | | Low | 10 | 20 | 40 | 60 | 80 | 100 |
| | | High | 20 | 40 | 60 | 80 | 100 | 120 |
| BG | | Ref. | 10 | 25 | 45 | 65 | 85 | 105 |
| Low | High | Ref. | Maximal Overshoot | | | | | |
| 40 | 70 | 55 | 130 | 160 | 160 | 160 | 160 | 160 |
| 70 | 100 | 85 | 145 | 160 | 160 | 160 | 160 | 160 |
| 100 | 130 | 115 | 145 | 160 | 160 | 160 | 160 | 160 |
| 130 | 160 | 145 | 145 | 160 | 160 | 160 | 160 | 160 |
| 160 | 190 | 175 | 145 | 160 | 160 | 160 | 160 | 160 |
| 190 | 220 | 205 | 145 | 160 | 160 | 160 | 160 | 160 |
| 220 | 250 | 235 | 145 | 160 | 160 | 160 | 160 | 160 |
| 250 | 280 | 265 | 145 | 160 | 160 | 160 | 160 | 160 |
| 280 | 310 | 295 | 145 | 160 | 160 | 160 | 160 | 160 |
| 310 | 340 | 325 | 145 | 160 | 160 | 160 | 160 | 160 |
| 340 | 370 | 355 | 145 | 160 | 160 | 160 | 160 | 160 |
| 370 | 400 | 385 | 145 | 160 | 160 | 160 | 160 | 160 |

FIG. 20c

METHOD FOR SELECTING BOLUS DOSES AND BOLUS DELIVERY PATTERNS IN A DRUG DELIVERY DEVICE

CROSS REFERENCE TO RELATED APPLICATIONS

The present application is a 35 U.S.C. §371 national stage entry of PCT/IL2009/000454, which has an international filing date of Apr. 28, 2009 and claims priority to U.S. provisional application No. 61/048,856, filed on Apr. 29, 2008, the entire disclosures of which are herein incorporated by reference in their entirety.

FIELD

Methods, systems and devices for sustained infusion of fluids are described. Some embodiments describe a portable infusion device and a method for selecting bolus dose and delivery pattern. Some embodiments describe, for example, a skin securable insulin dispensing device and a method for selecting bolus dose and delivery pattern according to carbohydrate load and content of the intake.

BACKGROUND

Diabetes mellitus is a disease of major global importance, increasing in frequency at almost epidemic rates, such that the worldwide prevalence in 2006 is 170 million people and predicted to at least double over the next 10-15 years. Diabetes is characterized by a chronically raised blood glucose concentration (hyperglycemia), due to a relative or absolute lack of the pancreatic hormone, insulin. Within the healthy pancreas, beta cells, located in the islets of Langerhans, continuously produce and secrete insulin according to the blood glucose levels, maintaining near constant glucose levels in the body.

Much of the burden of the disease to the patient and to health care resources is due to the long-term tissue complications, which affect both small blood vessels (microangiopathy, causing eye, kidney and nerve damage) and large blood vessels (causing accelerated atherosclerosis, with increased rates of coronary heart disease, peripheral vascular disease and stroke). The Diabetes Control and Complications Trial (DCCT) demonstrated that development and progression of the chronic complications of diabetes are greatly related to the degree of altered glycemia as quantified by determinations of glycohemoglobin (HbAlc). [DCCT Trial, N Engl J Med 1993; 329: 977-986, UKPDS Trial, Lancet 1998; 352: 837-853. BMJ 1998; 317, (7160): 703-13 and the EDIC Trial, N Engl J Med 2005; 353, (25): 2643-53]. Thus, maintaining normoglycemia by frequent glucose measurements and adjustment of insulin delivery accordingly is of utmost importance.

Insulin pumps have been available which can deliver rapidly acting insulin 24 hours a day, for example, through a cannula inserted subcutaneously. The total daily insulin dose can be divided into basal and bolus doses. Basal insulin dose or simply basal insulin can be delivered continuously over 24 hours, and keeps the blood glucose levels in an acceptable range between meals and overnight. Diurnal basal rates can be pre-programmed or manually changed according to various past or future daily activities.

Insulin bolus doses or simply boluses can be delivered to counteract carbohydrates loads before or after meals or during episodes of high blood sugar levels. The amount of insulin (bolus dose) can depend on several parameters that can be related to the intake, blood sugar, and patient's specific parameters including the following:

- an amount of carbohydrates (Carbs) in a meal to be consumed, alternatively defined as "servings", wherein 1 serving=15 grams of Carbs;
- carbohydrate-to-insulin ratio (CIR), i.e. the amount of carbohydrates balanced by one unit of insulin;
- insulin sensitivity (IS), i.e. the amount of blood glucose value lowered by one unit of insulin;
- current blood glucose level (CBG);
- target blood glucose level (TBG), i.e. the desired blood glucose level. TBG for most people suffering from diabetes is in the range of 90-130 mg/dL;
- residual insulin (RI), i.e. the amount of still active insulin remaining in the body after recent bolus deliveries. This parameter can be relevant in a situation when there is a short time interval between delivery of boluses (e.g. less than 5 hours); and
- parameters that influence carbs absorption and consequently rate of sugar rise in blood such as Glycemic Index (GI), fat or fibers content, etc.

The insulin sensitivity (IS) can be determined, for example, according to the so-called "2200 to 1600 rules" commonly used by type 1 diabetes patients using rapid acting insulin (e.g. Humalog®, Novolog®). The user's IS can be determined by dividing the value corresponding to a certain rule by the total daily dose of rapid-acting insulin. For example, if the total daily insulin dose is 40 units and the "1800" rule is used, the insulin sensitivity factor would be 1800 divided by 40=45 mg/dl/unit. FIG. 1 illustrates the insulin sensitivity expressed as point drop per unit of insulin corresponding to the various rules (adapted from Using Insulin written by John Walsh© 2003).

The carb to insulin ratio (CIR) can be determined, for example, according to the so-called "450 to 500 rules" commonly used by type 1 diabetes patients using rapid acting insulin (e.g. Humalog®, NovoLog®). The user CIR can be determined by dividing the value corresponding to a certain rule by the total daily dose of rapid-acting insulin. For example, if the total daily insulin dose is 40 units and the 450 rule is used, the carb to insulin ratio (CIR) would be 450 divided by 40=11 gram. FIG. 2 provides an example amount of carbs (in grams) that can be balanced by 1 unit of insulin (CIR) according to various rules (adapted from Using Insulin© 2003).

The residual insulin can be determined according to the pharmacokinetics of rapid acting insulin (e.g. Humalog®, NovoLog®). FIG. 3 illustrates one example of amount of residual insulin (in units) after 1-5 hours from a previous given bolus (adapted from Using Insulin© 2003).

The amount of insulin in the bolus to be delivered can be established by calculations using equations that include the abovementioned parameters, as described in U.S. Pat. No. 6,936,029 assigned to Medtronic MiniMed, or they can be selected by a method for selection of the desired bolus dose, as described in co-owned, co-pending U.S. patent application Ser. No. 12/051,400 and International Patent Application No. PCT/IL2008/000380, the disclosures of which are incorporated by reference in their entireties.

The bolus delivery pattern refers to a rate or rates at which the bolus dose is administered over time. The glycemic index (GI) or fat content of the intake influence carbs absorption and consequently bolus delivery time and pattern. The GI can be expressed as a ranking system for carbohydrates contained in food according to how they affect the blood glucose levels. Glucose, the fastest-acting carbohydrate, is given a value of 100, and the other carbs are ranked relative to that value.

Ripeness, cooking time, fiber, and fat content in the food can all impact GI. A low GI food will release glucose more slowly and steadily. A high GI food causes a more rapid rise in blood glucose. For example, FIG. 4 depicts different types of foods and their GI. A meal containing, for example, a carbohydrate load having high glycemic index (e.g. lemonade, white bread) would require insulin to be delivered immediately to counteract the carbohydrates rapidly absorbed through the gut. A meal containing a carbohydrate load having a low glycemic index (e.g. milk, ice cream) would require insulin to be delivered over a long period of time to counteract the slowly absorbed carbohydrates.

Currently, most insulin pumps allow the user to program the bolus delivery pattern. The most common delivery patterns are:
1. immediate ("regular", "normal") bolus—the entire bolus dose is delivered at the fastest pump delivery rate;
2. extended bolus—the entire bolus is delivered over a long period of time (e.g. 30 min-8 hours) at a constant rate; and
3. combined bolus ("dual wave")—some of the bolus dose is delivered as an immediate bolus and the rest of the bolus dose is delivered as an extended bolus. Usually the ratio (in percentage) between the immediate bolus portion and the extended bolus portion can be selected by the patient, e.g. as described in U.S. Pat. No. 6,852,104 assigned to Smiths Medical MD (formerly Deltec Medical).

In current devices, in order to adjust a bolus delivery pattern, a user can program one or more of the following parameters: duration of bolus delivery (for extended bolus and extended portion of a combined bolus), ratio between the immediate bolus portion and extended bolus portion (for combined bolus). In practice, a user's decision about the bolus pattern is arbitrary and based merely on intuition. Additional drawbacks associated with conventional pumps that include means for programming bolus pattern are:
the necessity for data input which complicates the user interface because it requires navigation through several displays which are not user-friendly; and
difficulties for young children may to master data input since it is associated with reading and typing alphanumeric parameters.

The following definitions are provided for terms used herein:
"GI" (Glycemic Index) refers to a ranking system for carbohydrates based on how they affect blood glucose levels.
"GL" (Glycemic Load") refers to the amount of carbs in a meal multiplied by the GI of the meal divided by 100.
"CIR" (Carbohydrate to Insulin Ratio) refers to the amount of carbohydrates balanced by one unit of insulin.
"IS" (Insulin Sensitivity) refers to the amount of blood glucose value lowered by one unit of insulin.
"Dose" or "bolus dose" refers to amount of insulin administered to counteract carbohydrates in a meal (for example 6 units (6 U)).
"Delivery pattern" refers to the pattern of delivery over time of administered dose (for example a dose of 6 U may be delivered as follow—4 U in 2 hours and 2 U in additional 4 hours).
"Bolus" refers to the combination of bolus dose and delivery pattern.
"Grid" or "bolus grid" refers to a matrix of 2 or more dimensions constructed of cells. (for example a 3D matrix including the following axes: X—carbs, Y—blood glucose, Z—glycemic index) Each grid is dedicated to a different combination of parameters like CIR, IS, and target blood glucose (TBG).
"Cell" refers to one of many units comprising a grid. Each cell represents a combination of parameters exhibited on the different axes of the grid (e.g. combination of ranges of GI, BG, and carb load).

SUMMARY

Embodiments of the present disclosure relate to techniques, systems and devices are described for drug delivery according to selected drug dose and drug delivery pattern. For example, according to some embodiments, a drug delivery system and device is provided which includes some embodiments of a user interface for selection of one or more bolus configurations. In addition, one or more user interface elements may be included where each user interface element corresponds to a bolus configuration. Moreover, in some embodiments, each element is spatially positioned within a multi-dimensional space corresponding to at least three dimensions, where the element's position, in some embodiments, corresponds to each dimension. In such embodiments, each bolus configuration can correspond to a bolus dose and a bolus delivery pattern. Moreover, each bolus dose and/or each bolus delivery pattern can be pre-determined. For example, some embodiments of the delivered drug can be insulin and the drug delivery device can be an insulin pump. The dimensions of the multi-dimensional space can represent at least one or more of, and preferably at least three of, for example, the current blood glucose levels, anticipated or current carbohydrate load of the intake, glycemic index of the intake, and glycemic load of the intake. The bolus dose can be recommended in accordance with the carbohydrate load of the intake and the blood glucose level of the user, and the bolus delivery pattern can be recommended in accordance with the content of the intake (e.g. GI, fiber content, fat content). The bolus dose and/or delivery pattern can be further in accordance with one or more physiological parameters. In some embodiments, the physiological parameters can correspond to at least one of a heart rate, a ventilation rate, a body temperature, insulin absorption characteristics (e.g. rate), physical activity (e.g. exercise, steps of the user per period of time.

In some embodiments, the delivery pattern can be recommended according to the GI of the intake. The bolus delivery pattern can be recommended in accordance with a correction bolus. In some embodiments, the measurements of the dimensions can be represented as qualitative descriptive parameters. The qualitative descriptive parameters can comprise one or more ranges. The ranges can be selected, for example, from the group of small, medium and large.

The drug delivery system and/or device can further comprise a glucometer. The user interface of the drug delivery device can be implemented in the system via a remote control unit and the drug can be delivered using a skin securable patch unit. The glucometer can be located in the remote control unit of the device and/or in the skin securable patch unit of the device. The drug delivery device can also comprise a continuous glucose monitor. The continuous glucose monitor can be located in the patch unit of the device, and/or in the remote (in some embodiments, components of the continuous glucose monitor may be provided in the remote).

In some embodiments, the insulin bolus delivery pattern can be determined as a function of a fat content of the food intake. The insulin bolus delivery pattern can also be established as a function of a fiber content of the food intake. In some embodiments, the bolus doses do not exceed a predetermined maximal overshoot and minimal undershoot criteria. The maximal overshoot and minimal undershoot criteria can be defined by the user.

In some embodiments, the drug delivery system and/or device can also comprise a second user interface for displaying user interface elements positioned within a two-dimensional space and the two dimensions of the two-dimensional space correspond to at least two dimensions of the multi-dimensional space. In some embodiments, the drug delivery device can also comprise a disposable part and a reusable part. It can comprise a skin securable cradle unit allowing disconnection and reconnection of the patch unit.

BRIEF DESCRIPTION OF THE DRAWINGS

FIG. 1 is a table for calculating insulin sensitivity (point drop per unit of insulin) according to various rules.

FIG. 2 is a table for calculating CIR (carbs in grams balanced by 1 unit of insulin) according to various rules.

FIG. 3 is a table for calculating Residual Insulin (in units) after 1-5 hours from a previous given bolus.

FIG. 4 is a chart depicting different types of foods and their GI ranking system based on how they affect blood glucose levels.

FIGS. 11a-d illustrate "two dimensional" slices of the three dimensional bolus-grids with insulin bolus dosages and delivery patterns corresponding to carb load, GI, and current blood glucose levels, yielding a 2D chart, according to some embodiments.

FIGS. 16a-c provide some examples of an insulin infusion system/device containing blood glucose monitor providing blood glucose (BG) readings for the bolus selector, according to some embodiments of the present disclosure.

FIGS. 17a-b provide examples of insulin infusion system/device containing various subcutaneous glucose monitors providing blood glucose readings (BG) for the bolus selector, according to some embodiments of the present disclosure.

FIGS. 20a-c illustrate examples of 2D slices derived from a 3D bolus grid with its corresponding minimal undershoot and maximal overshoot BG values, according to some embodiments of the present disclosure.

DETAILED DESCRIPTION

Systems, devices and methods for selecting, for example, a drug bolus dose and a bolus delivery pattern are provided herein. In some embodiment, the device can comprise a user interface for selection of one or more bolus configurations. The bolus configurations can be selected using one or more user interface elements (for example).

In some embodiments, each user interface element can correspond to a bolus configuration. For example, each user interface element can be spatially positioned within a multi-dimensional space. In some embodiments, the multi-dimensional space corresponds to at least three dimensions. The spatial position of the user interface elements within the multi-dimensional space can correspond to each dimension.

In some embodiments, a three-dimensional matrix of cells can be used to recommend pre-determined insulin boluses that are pre-determined for each combination of carbs load of the intake, GI of the intake and BG of the user. In that implementation, each cell can represent a user interface element and can correspond to a bolus configuration (for example. These bolus configurations can be pre-determined and stored in a memory of the bolus selector. In some embodiments, these bolus configurations can be predetermined by a manufacturer, a parent, a physician and/or by a user. The pre-determined database can be displayed by the bolus selector graphically as a plurality of cells arranged in a 3D grid, referred-to as a "bolus-grid."

Figures 5, 6:
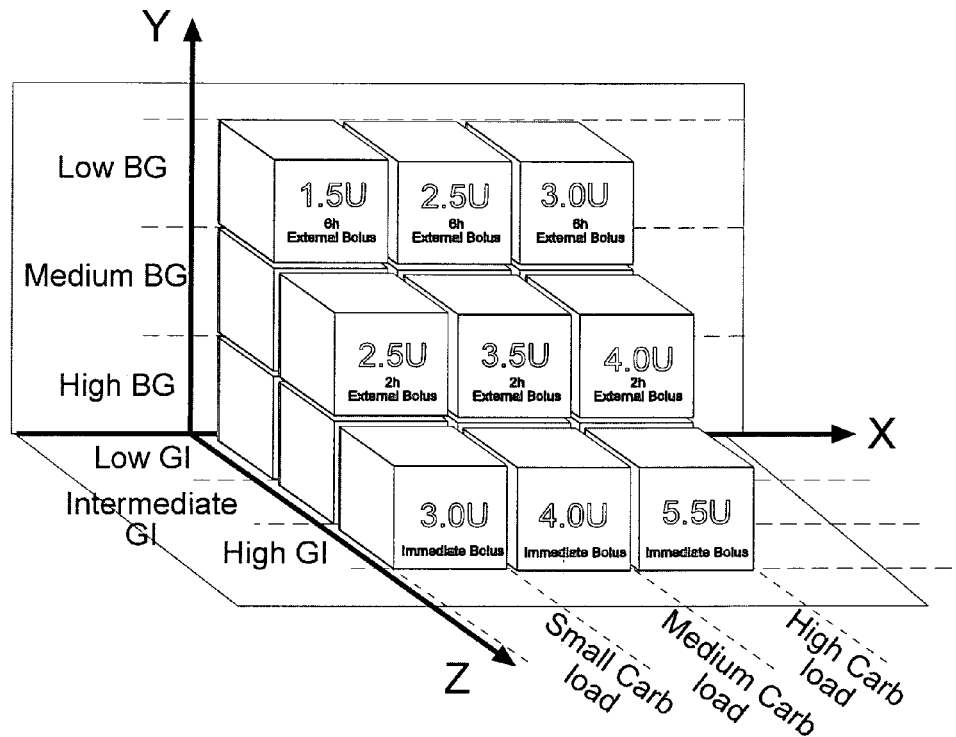
FIG. 5 provides one example of a three-dimensional grid, where carbohydrate intake ranges are presented on the "x" axis of the grid, blood glucose levels (BG) are presented on the "y" axis of the grid, and GI levels are presented on the "z" axis of the grid, according to some embodiments of the present disclosure.
FIG. 6 provides one example of a 2D bolus-grid that illustrates delivery patterns selected for High BG range and various values of GI and Carb loads according to some embodiments of the present disclosure.

FIG. 5 illustrates a simplified example of a 3-dimensional grid of the bolus selector. Carbohydrate intake ranges are presented on the "x" axis of the grid, blood glucose levels (BG) are presented on the "y" axis of the grid, and GI levels are presented on the "z" axis of the grid. Any other parameter that, for example, expresses a characteristics of the intake that determine its absorption (e.g. fat content, fiber content, cooking time), can be presented on the "z" axis of the grid. The bolus-grid can also allow the user to select a cell from within the bolus-grid depending on a combination of ranges of BG, carbohydrate load of the intake, and GI of the intake (for example).

Accordingly, in some embodiments, the dose of the bolus can be selected from the pre-determined combination ("grids") of carbohydrate loads and BG that pre-define a value of insulin dose. For example, the intersection of the "x" (carb load) and "y" (BG) axes of the grid can corresponds to a pre-determined bolus dose.

The delivery pattern of the bolus can be selected according to the meal content. For example, the glycemic index of the meal. Thus; for example, the intersection of the "z" axis (GI) with the bolus dose (as derived from the intersection of the "x" and "y" axes), correspond to the final selected bolus—dose and delivery pattern. The following list provides a few examples of the delivery patterns:

1—entire dose delivered immediately;
2—portion of dose delivered immediately and the rest over 2 hours;
3—portion of dose delivered immediately and the rest over 4 hours;
4—entire dose delivered over 6 hours.

In some embodiments, the user can also select, for example, the insulin bolus dose from a pre-determined three dimensional grid of insulin boluses, corresponding to given ranges of blood glucose (BG) values (e.g. BG<100, 100<BG<200, 200<BG<300, 300<BG), ranges of carbohydrate loads (e.g. carbs<45, 45<carbs<105, carbs<105) and given ranges of glycemic loads (e.g. GL<10, 11<GL<19, GL>20). The delivery pattern can be determined, for example, according to the glycemic load of the intake.

According to some embodiments, a three dimensional bolus grid may comprise BG ranges, carb load ranges and GI ranges. For example, the GL can be automatically calculated according to the selected GI range and carb load range. The delivery pattern can be subsequently selected according to the calculated GL, for example. GL can also be pre-determined for each combination of GI and carb load.

According to some embodiments, the carb load ranges can be presented on the axis of the grid in servings instead of grams. One serving of a carbohydrate food typically contains 15 grams of carbohydrate (e.g. serving<3, 3<servings<7, serving>7), rather than distinct values.

In some embodiments, the bolus selector can include the ability for a user to insert the numerical value of blood glucose instead of selecting a range of BG levels. The BG numerical value can then be ascribed by the bolus selector to the relevant range of BG levels. For example, if the user inserts a BG of 221 mg/dL, the bolus selector automatically assigns the numerical value to the relevant BG range: 210-230 mg/dL.

In some embodiments, the pre-determined insulin doses that correspond to a selected current BG range and carbohydrate load intake range can be pre-determined according to a formula which takes into consideration the user's CIR, IS, and target blood glucose (TBG) as constant coefficients. The bolus selector can comprise a plurality of grids, and each grid can correspond to a different combination of user specific parameters that may include IS, CIR, and TBG.

The plurality of 3D bolus grids can be stored in the memory of the bolus selector and each grid can correspond to a different combination of IS, CIR, and TBG. By virtue of this provision, the bolus-grid doses are adjusted to the user's individual insulin needs as dictated by the user's specific CIR, IS, and TBG. Each grid in the bolus selector can be configured for a different combination of CIR, IS, and TBG. The user can insert the TBG, CIR, and IS values when initially setting the bolus selector in order for the appropriate grid to be retrieved.

Alternatively, according to some embodiments, the user can provide a "rule" and a total daily dose (TDD), and the CIR and IS value can subsequently be obtained (as shown in FIGS. 1 and 2). For example, the user can provide the following information in the initial setting:

"Rule" for CIR=500

TDD=25 U

"Rule" for IS=2000

Using the example values presented above and the tables on FIG. 1 and FIG. 2, the CIR value is 20 g/U (CIR=500/25) and the IS value is 80 mg/dL/U (2000/25).

In some embodiments, additional parameters, such as time lapsed from last meals and amount of previous bolus doses, can be taken into consideration for recommending a final bolus dose. For example, the amount of residual insulin can be subtracted from the insulin dose recommended by the bolus selector, resulting in a lower recommended bolus dose (e.g. if the user has 2 U of residual insulin from previous boluses and according to the bolus selector grid an insulin dose of 4 U is required to balance a contemplated meal, than the final recommendation would be 4−2=2 U).

In some embodiments, the recommended bolus (dose and delivery pattern) can be selected by the user from a displayed three dimensional graph wherein one axis can indicate ranges of current BG levels, one axis can indicate ranges of carbohydrate loads, and a third axis can indicate ranges of GI or GL, for example.

In some embodiments, the recommended bolus dose can be automatically selected by the bolus selector upon inputs of at least a range of current BG levels, a range of carbohydrate load, and a range of GI or GL. That is, the cell of the grid that is the intersection of the parameters inputted by the user is automatically selected.

In some embodiments, the user can accept the bolus automatically selected and recommended upon inputs of at least a range of current BG levels, a range of carbohydrate load, and a range of GI or GL, and can deliver a bolus accordingly. In addition, the automatically selected bolus can be delivered without providing a notification to a user interface. In such an embodiment, the user can be notified prior to bolus administration and can suspend delivery or select an alternative dose and/or delivery pattern.

In some embodiments, a bolus selector can be constructed of "n" dimensions. For example, each dimension can represent an independent parameter that influences the optimal bolus to be delivered. The dose and delivery pattern of the bolus can thus be selected from pre-determined grids of "n" dimensions. For example, a 4 dimensional grid can comprise a "v" axis representing the user's BG, a "w" axis representing the carbohydrate load, a "x" axis representing the GI of the intake, a "y" axis representing the fat content of the intake, and a "z" axis representing the fiber content of the intake. The intersection of all 4 axes correspond to the final selected bolus—dose and delivery pattern.

Some embodiments according to the present disclosure disclose a portable drug delivery system/device that can deliver therapeutic fluids into the body (i.e. insulin). In some embodiments, it can also monitor bodily analyte levels (i.e. glucose). The drug delivery system can comprise a dispensing patch unit and, in some embodiments, can be combined with a remote control unit, which communicates with the dispensing patch unit and allows programming of therapeutic fluid delivery, user input and data acquisition. In another embodiment, programming can be carried out manually by operating buttons located on the dispensing patch unit.

The dispensing patch unit can be composed of two parts—a disposable part and a reusable part. The disposable part can contain reservoir, outlet port, and other relatively inexpensive components. The reusable part can contain electronics (PCB, processor, etc), driving mechanism (e.g. a motor, gears) and other relatively expensive components (e.g. occlusion sensor). A cradle unit can be provided, which is an element (e.g., a substantially flat sheet of material) that adheres to the skin and allows disconnection and reconnection of the patch unit (sometimes referred to as a dispensing unit or dispensing patch unit) upon patient discretion. After attachment of the cradle unit to the skin, a cannula can be inserted into the subcutaneous compartment through a dedicated passageway in the cradle unit. The described drug delivery device can be provided with a software feature enabling selecting an appropriate bolus dose and delivery pattern.

In some embodiments, the drug delivery device can employ a simplified, easy to use method for selecting appropriate insulin bolus from a plurality of pre-determined insulin bolus doses and bolus delivery patterns. For example, such method can be used with a device dedicated for selection of the appropriate bolus, or it can be implemented in a glucometer, a continuous glucose monitor, an infusion pump, a delivery pen, a PC or any other device used by the diabetes patient.

In some embodiments, the drug delivery system/device can continuously monitor body glucose levels and can concomitantly deliver insulin boluses. Some embodiments of the present disclosure can provide a device comprising a miniature skin securable insulin dispensing patch that can deliver insulin boluses according to bolus selecting method.

Some embodiments can provide a device that includes a skin securable dispensing patch unit and a method to select an insulin bolus. The dispensing patch unit can be attached to the skin directly, or by virtue of a cradle unit. Some embodiments provide a device with a dispensing patch unit that can be disconnected and reconnected and a method to select an insulin bolus. Some embodiments provide a device comprising a miniature skin securable patch that can continuously dispense insulin and monitor body glucose concentration levels and a method to select an insulin bolus. In some embodiments, the patch can be secured using an adhesive substance or a strap.

Some embodiments provide a device that dispenses insulin according to monitored glucose levels (semi closed loop system) and a method to select an insulin bolus. In some embodiments, the device can comprise insulin dispensing patch unit that can be remotely controlled and a method to select an insulin bolus.

In some embodiments, the method(s) for selecting a bolus can employ at least one of the following parameters: current blood glucose levels (BG), carbohydrate load of the intake (Carb), glycemic index of the intake (GI), glycemic load of the intake (GL).

In some embodiments, the method for insulin bolus delivery can be based on selection of the optimal dose from a database of pre-determined values of bolus doses and on selection of the optimal bolus delivery pattern from a database of pre-determined bolus delivery patterns.

In one embodiment, the user can select the insulin bolus dose from a pre-determined three dimensional grid of insulin boluses, corresponding to ranges of blood glucose (BG) values (e.g. BG<100, 100<BG<200, 200<BG<300, 300<BG), ranges of carbohydrate loads (e.g. carbs<45, 45<carbs<105, carbs<105) and ranges of glycemic indexes (e.g. GI<55, 56<GI<69, GI>70).

According to some examples, ranges of blood glucose level, glycemic index of the intake, and carbohydrate load of the intake are presented on the axes of the grid as a qualitative descriptive parameter (QDP) (e.g. high/medium/low BG, high/intermediate/low GI, small/medium/large carb load).

In some embodiments, the bolus selection method can be implemented in an insulin infusion system comprising an insulin dispensing patch unit and a remote control unit, where a blood glucose sensing apparatus (e.g. glucometer) can be integrated in the remote control unit (while it may also be integrated into the patch unit, for example). In one such embodiment, the dispensing patch unit can be composed of two parts, a reusable part that can contain all electronic and driving elements and a disposable part that can contain insulin reservoir and power supply. The blood glucose sensing apparatus (e.g. glucometer) can alternatively be integrated in the reusable part of the patch unit of the device.

In some embodiments, the blood glucose sensing apparatus such as a glucometer, can be dedicated for measuring glucose concentrations. For example, it can be implemented as a "stand-alone" device, an element in the remote control, which receives blood strips, a sensor in the housing of the dispensing unit such as electrodes disposed on the cannula, etc, as disclosed in co-owned, co pending U.S. patent application Ser. Nos. 11/706,606 and 11/963,481, in International Patent Application Nos. PCT/IL2007/001579 and PCT/IL2008/001521, the disclosures of which are incorporated by reference in their entireties. It can also be implemented as a continuous glucose monitor (CGM). It can use various techniques such as an electrochemical means (e.g. electrochemical sensors, electrodes, enzymes, nanoparticles), an optical means (e.g. optical sensors, optical fibers, reflectors, mirrors, lens), an acoustic means etc. It can measure the glucose level in the blood, interstitial fluid ("ISF") or any other relevant compartment of the patient's body.

The bolus selector can be implemented in the remote control unit of the insulin infusion system. The bolus selector can also be implemented in the reusable part of the dispensing patch unit of the device of the system. The bolus selector can be implemented in both the reusable part of the dispensing patch unit of the device and the remote control unit of the system.

In one embodiment, the bolus selection method can be implemented in the dispensing patch unit that can continuously monitor body glucose levels and can concomitantly deliver insulin into the body. The dispensing patch unit can comprise a reusable part and a disposable part. The insulin dispensing and glucose sensing capabilities can be combined into a semi closed loop system, where a processor-controller apparatus regulates the dispensing of basal insulin according to the sensed glucose concentration. The meal boluses can be controlled by the bolus selector.

The bolus selector can be implemented in the remote control unit of the system, and/or can also be implemented in the reusable part of dispensing patch unit of the device. In some embodiments, the bolus selection method can be implemented in a device for sensing blood glucose (e.g. glucometer) or a device for continuously sensing subcutaneous interstitial fluid glucose or for any other glucose sensing device (i.e. non invasive glucose sensors, iontopheresis based sensors, etc.)

In some embodiments, the delivery pattern of the insulin dose can be selected by the user according to the glycemic index (GI) or glycemic indexes of the carbohydrates of the intake. The delivery pattern of the insulin dose can also be selected by the user according to the glycemic load (GL) of the carbohydrates contained in the intake. The GL of a meal is defined as GL=(GI*carb load)/100. The duration of insulin action (DIA) can be affected by the size of the insulin dose, with higher doses correlated with a longer DIA. Therefore, the size of the dose which reflects the carbohydrate load of the meal, should also influences the delivery pattern (long DIA requires a longer delivery profile and vice versa).

The delivery pattern of the insulin dose can alternatively be selected by the user according to additional characteristics of the intake such as the fat content, fiber content, or cooking time. For instance, a high fat meal will slow down glucose absorption from the gut and thus require a relatively long bolus delivery pattern to match the glucose absorption rate.

FIG. 6 illustrates one example of a 2D bolus-grid that illustrates delivery patterns selected for High BG range and various values of GI and Carb loads. The user can insert a numerical BG value (that can automatically be ascribed by the bolus selector to the relevant range of BG levels) or select a BG range and subsequently a 2D matrix, as shown in the figure, can be displayed to the user. For example, if the user's measured BG is 225, then the pre-determined bolus grid matrix corresponding to the High BG can be displayed.

Figure 7:
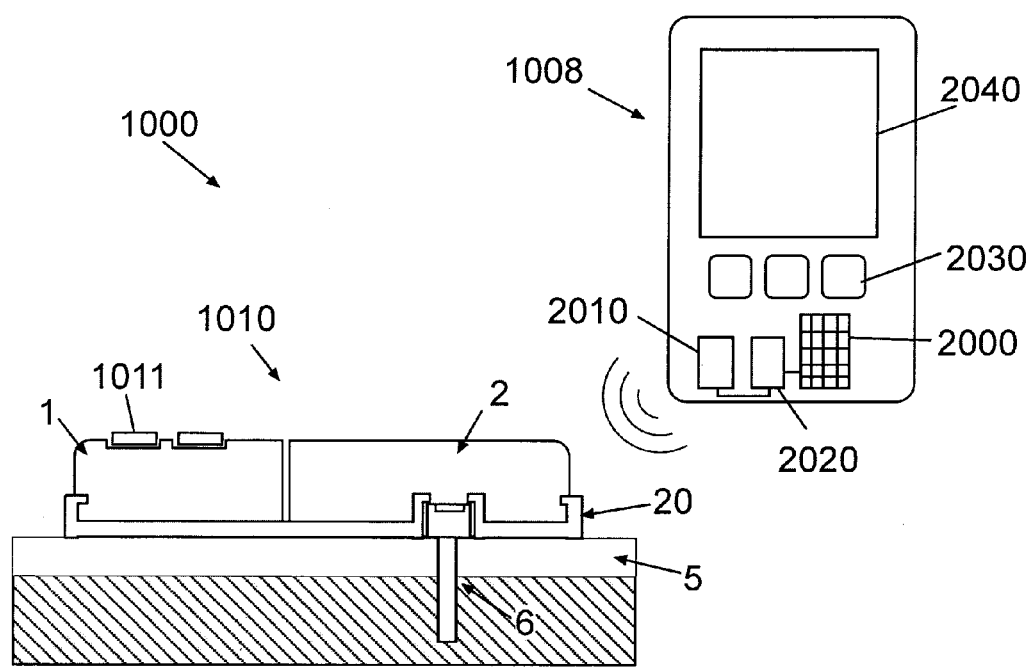
FIG. 7 is a diagram illustrating an example of an insulin infusion system comprising an insulin dispensing unit and a remote control unit that can be fitted with a bolus selector, according to some embodiments of the disclosure.

FIG. 7 illustrates an insulin infusion device (1000) comprising a dispensing patch unit (hereinafter "patch unit") (1010), which can be adhered to the user's skin (5), and a remote control unit (1008), which communicates with the dispensing patch unit (1010), allowing programming, user inputs and data acquisition. The patch unit (1010) can be removably connected to a cannula (6) that can penetrate the skin (5) to allow delivery of insulin to the patient. The patch unit (1010) can be attached to a dedicated cradle unit (20) that can be configured as a substantially flat sheet adhered to the user's skin (5). The cradle unit can allows connection/disconnection of the patch unit (1010). An exemplary embodiment of this arrangement is discussed in a co-owned, co-pending U.S. patent application Ser. No. 12/004,837 and International Patent Application No. PCT/IL07/001578, the disclosures of which are herein incorporated by reference in their entireties.

Manual inputs can be effected by one or more buttons/switches (1011) located on the dispensing patch unit (1010). The dispensing patch unit (1010) can be fitted with one housing or two housings comprising reusable (1) and disposable (2) parts as shown in co-owned, co-pending patent application U.S. Ser. No. 11/397,115 and International Patent Application No. PCT/IL2009/000388, the disclosures of which are incorporated by reference in their entireties. The remote control unit (1008) can contain a bolus selector (2000), which can be implemented as a software feature. The remote control unit (1008) can comprise a processor (2010), a memory (2020), an input means (2030) such as buttons, switches, touch-screen, voice/audible commander/receiver, a display (2040) and other indication means such as, for example, audible means (e.g. buzzer) and/or vibration means (e.g. vibrator). The input means (2030) can be provided for the bolus selector (2000) and for dispensing patch unit (1010) programming.

Options for insulin bolus administration can be provided by the bolus selector (2000) on the display (2040) as a three dimensional grid with cells containing recommended pre-determined bolus dosages and recommended pre-determined delivery patterns. The appropriate cell and corresponding insulin dose and delivery pattern can be selected from a pre-determined 3D table according to, for example, at least one parameter selected from blood glucose, carb content, and GI or GL. A 3D bolus grid can, for example, include the following axes: X—carbs, Y—blood glucose, Z—glycemic index. For example, each intersection of the X and Y axes can define a bolus dose. Each intersection of a bolus dose with the Z axis can define the delivery pattern at which the bolus dose is to be administered. Such a table with recommended pre-determined bolus dosages and recommended pre-determined delivery patterns will be referred-to further as a "bolus-grid" and any combination of two or more grids will be referred-to further as a "bolus-grid cell" or a "cell".

The bolus-grid cells can comprise pre-determined bolus doses and delivery patterns corresponding to optional combinations of the current blood glucose level, the user's approximation of the carb load in the consumed or to be consumed meal, and the user's approximation of the GI or the GL of the consumed or to be consumed meal (examples of such grids are shown in FIGS. 5 and 6). In some embodiments, the bolus-grids can be pre-determined and stored in the memory of the bolus selector (2000).

In some embodiments, the bolus selector (2000) can contain many 3D bolus grids. Each grid can correspond to a specific combination of the target BG, IS value, and CIR. The user's specific bolus-grid or grids (e.g. a user has different TBG throughout the day) can be retrievable from the bolus selector (2000) memory, for example. In some embodiments, the bolus selector can be located in the reusable part of the dispensing patch unit.

Figure 8:
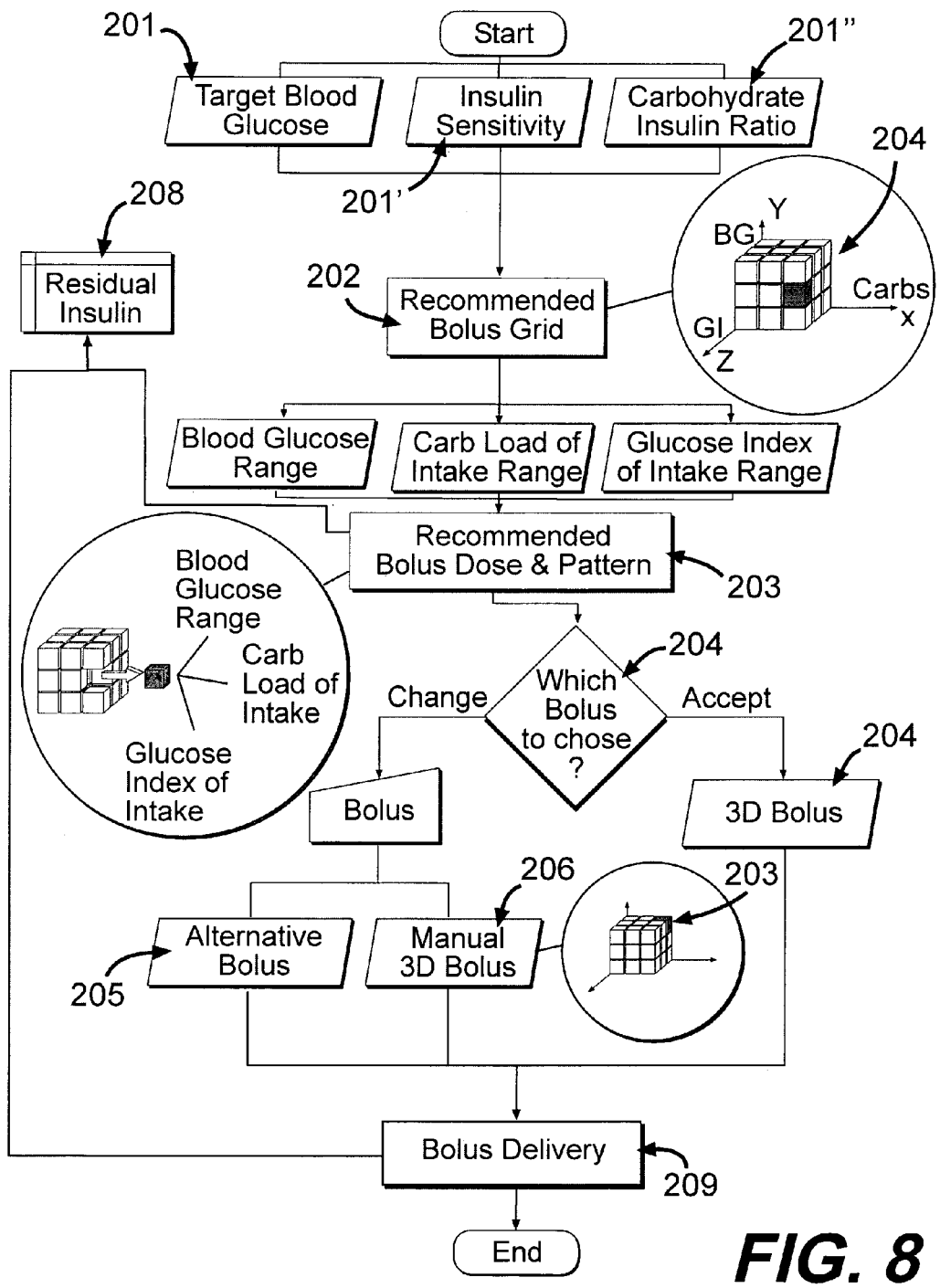
FIG. 8 is a flow chart representing some embodiments of a method for selecting a recommended insulin bolus (dosage and delivery pattern) according to some embodiments of the present disclosure.

FIG. 8 illustrates a block diagram representing one example of the method for selecting a recommended insulin bolus dosage and a recommended delivery pattern. For example, this method can be implemented by the bolus selector. In some embodiments, for selection of the user specific bolus, a three dimensional grid with pre-established insulin boluses can be retrieved from the memory of the bolus selector. A plurality of grids can also be saved in the memory of the bolus selector. Each grid can be suitable for a different combination of user specific parameters, such as IS, CIR, and TBG. The appropriate grid can be retrieved from the memory upon user input of these parameters.

The bolus can be pre-determined for each combination of carb load, GI, and blood glucose level in each stored bolus-grid. The user can select the appropriate combination of these parameters, input them into the bolus selector and, in some embodiments, automatically retrieve a cell of the grid corresponding to this combination. This cell can provide a bolus describing a dose and a delivery pattern from the retrieved bolus-grid. The appropriate bolus should correspond to a combination of the contemplated carb intake (load and GI) and results of the actual measurements of the blood glucose level. The measurements of the blood glucose level can be inputted by the user or automatically obtained from a glucometer or a continuous glucose monitor (CGM) that, in some embodiments, communicates with the bolus selector. The bolus delivery patterns can also be pre-determined according to a series of tests for tailoring the GI related delivery bolus to a user. These tests can be performed by the user during the initial setting of the infusion device.

In some embodiments, IS, CIR and target BG values (designated in FIG. 8 as 201,201',201", for example) can be loaded in the bolus selector by the patient, and the patient's specific bolus-grid can be retrieved accordingly at (202) and displayed to the patient. At 203, the recommended bolus from the displayed bolus-grid can be selected. The selection can be based on the contemplated carb load of the intake, GI of the intake and/or blood glucose (BG) level (for example). These parameters can be presented within the bolus-grid, in this example "x" axis—carb ranges, "y" axis—BG ranges, and "z" axis—GI ranges. Selection of the relevant combination of these parameters is designated as (204).

Blood glucose levels can be obtained from any suitable glucose sensor e.g. glucometer, continuous subcutaneous glucose sensor etc. Glucose measurements can be carried out immediately before the bolus selection. Contemplated carb load and GI can be assessed by the user.

In some embodiments, for example as shown at (208), the residual insulin value can be obtained from the previous bolus doses and elapsed time (e.g., as shown in FIG. 3). The input of the residual insulin value can trigger subtraction of the residual insulin content from the recommended bolus dose. For example, as illustrated in FIG. 3, if 2 units of insulin were administered 1 hour prior to administering of the current bolus, 1.6 units of insulin were not absorbed and reside in the body (residual insulin=1.6). Therefore, the bolus suggested by the bolus selector should be lower by 1.6 units than the pre-determined bolus with no residual insulin (residual insulin=0). Moreover, if 2 units of insulin were administered 1 hour prior to the current bolus (1.6 U) and 3 units were administered 3 hours prior to the current bolus (RI=1.2 U), 2.8 U (1.2+1.6) should be subtracted (for example). In some embodiments, the residual insulin does not affect the delivery bolus pattern, just the dose. Various infusion devices can be used for insulin delivery (e.g., insulin pumps, injection pens, delivery/dispensing devices, etc). Insulin residue values can be displayed periodically or at the user's discretion (for example).

According to another embodiment, the RI can be an additional dimension of the bolus grid, for example. That is, an axis with ranges of RI can also be a parameter in determining the cell with the recommended bolus dose and delivery pattern. In such an embodiment, there is no subtraction of RI but rather a selection of RI.

At (204), the user can accept the selected bolus dose and delivery pattern. In some embodiments, for example as shown at 206, the user can manually modify the selected bolus by navigating across the bolus-grid and retrieving an alternative bolus (alternative dose and/or delivery pattern).

At (205), a user can substitute the selected bolus with an alternative bolus (not from the bolus-grid), according to some embodiments. Irrespective of whether the bolus is selected by the bolus selector at (204), or modified and selected at (206), or chosen at (205), the bolus delivery can be initiated at (209) by a command transmitted from the remote control unit and/or by manual bolus buttons that can be located on the dispensing patch unit.

In one embodiment, the axes (e.g. carbohydrate intake ranges are presented on the "x" axis of the grid, blood glucose levels are presented on the "y" axis of the grid, and the GL levels are presented on the "z" axis of the grid) of the 3D bolus-grids can comprise preset ranges of carb load, ranges of GL, and ranges of blood glucose level. The boluses can be pre-determined for each combination of carb load range, GL range and a range of blood glucose level.

In some embodiments, the axes of the 3D bolus-grids can comprise ranges of carb load, ranges of GI and ranges of blood glucose level. In some embodiments, the ranges of GL are not pre-determined, but are calculated by the bolus selector from the selected range of GI and range of carb load. For example, the boluses can be pre-determined for each combination of carb load range, calculated GL range, and range of blood glucose level.

Figure 9:
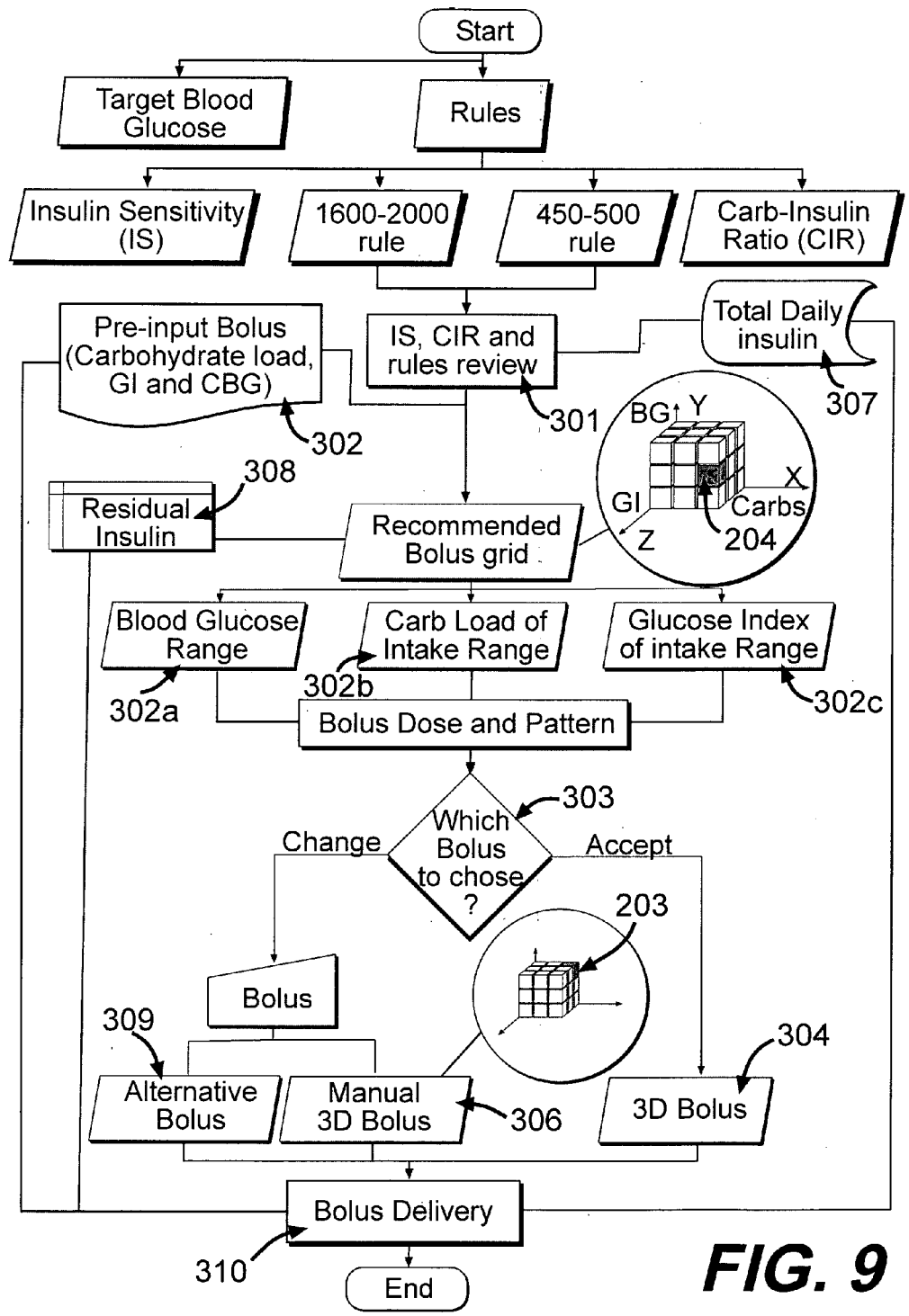
FIG. 9 is a flow chart representing another example of a method for selecting a recommended insulin bolus according to some embodiments of the present disclosure.

FIG. 9 illustrates a block diagram of a bolus selector, according to some embodiments, that can be used for implementing the method for selecting a recommended insulin bolus. At 301, for example, the bolus selector can be preset according to the user's individual parameters—i.e. the following parameters are set: carbohydrate to insulin ratio (CIR) and insulin sensitivity (IS). These parameters can be obtained by the "450-500 rules" and "1600 to 2200 rules" respectively (e.g. as illustrated on FIGS. 1 and 2).

In some embodiments, the user can preset an additional parameter, namely the target blood glucose (TBG) levels. TBG can vary throughout the day and this parameter can be configurable to allow retrieval of the pre-meal appropriate bolus-grid. The IS value and the CIR can also vary throughout the day and these parameters can also be configurable to allow retrieval of the pre-meal appropriate bolus-grid.

In some embodiments, the CIR and IS values can repeatedly be adjusted according to the recently (e.g. last days) stored bolus data. This step can be designated as step (307). CIR and IS values can be selected from Tables 2 and 1 respectively by choosing the appropriate rule and a total daily dose (TDD), which, in on implementation, can be an average from the last days' usage data. For example, if the 500 and 1800 rules are selected and the average TDD is 50 IU/day, the CIR and IS are 10 gram/unit and 36 mg/dl/unit respectively. After adjustment of the CIR and IS values, appropriate bolus-grids corresponding to the revised IS and CIR parameters can be retrieved by the bolus selector.

In some embodiments, the rules applied can also be repeatedly adjusted according to the last days stored bolus data. For example, the rules can be associated with the percentage of the basal dose from the total daily dose (TDD). The optimal rules to be applied can, therefore, be determined by establishing the percentage of the basal dose from the stored total daily dose (TDD). For example, if the basal dose is 50% of the TDD, the optimal applied rules should be the "500 rule" and "2000 rule" for the CIR and IS respectively. If the basal dose is 40% of the TDD, the applied rules should be the "450 rule" and "1800 rule" for the CIR and IS respectively. If the basal dose is 60% of the TDD, the applied rules should be the "550 rule" and "2200 rule" for the CIR and IS respectively.

Step 302 can be an optional feature of the bolus selector according to some embodiments. This feature which can shorten the time of the selection process by presenting the average bolus dose and delivery pattern used during a selected time interval in the last few days to the user. For example, the day can be divided into five time intervals (e.g. 6:00-10:00, 10:00-14:00, 14:00-18:00. 18:00-22:00, 22:00-6:00) and the average of the total amount of insulin and the most prevalent delivery pattern delivered during the corresponding time interval in the last several days would be the featured value (302). The bolus selector can thus indicate a bolus even prior to loading the BG, carbs load and GI. This value can be displayed as a stand alone parameter or as a first preferable choice or marked cell within the 3D bolus grid and it can be used as an adjunct recommendation for bolus selection.

The defined time interval can also be selected from a certain basal profile (e.g. by averaging the boluses given between 6 to 10 am in the last 7 "weekend" profiles), for example.

In one embodiment, the averaged bolus dose can be presented to the user if the standard deviation of the bolus dose is insignificant. If a significant deviation is noted, the averaged bolus dose value is not presented. The bolus selector can also alert the user if the selected bolus differs from the average value by, for example, a considerable amount. A considerable amount can be defined as percentage of the total bolus dose. Alternatively, a considerable amount can be individually defined for each user according to the user's IS value. For example, a deviation of 1 unit for a user with an IS of 90 mg/dL/U may cause a BG drop of 90 mg/dL, wherein a deviation of 1 unit for a user with an IS of 10 mg/dL/U may cause a BG drop of 10 mg/dL.

The data referring to the time, the dosage, and the delivery pattern of the previously administered boluses can be stored in the memory (2020), as shown in FIG. 7, and can be displayed periodically or at the user's discretion, according to some embodiments of the present disclosure.

At 303, the bolus dose from the retrieved bolus-grid can be selected. In this example, "x" axis represents carb ranges, "y" axis represents BG ranges, and "z" axis represents GI ranges (204). Blood glucose levels can be obtained at the step (302a) from any suitable glucose sensor e.g. glucometer, continuous subcutaneous glucose sensor etc. The carb load and GI can be evaluated by the user at steps (302b) and (302c) respectively. At 308, the residual insulin content can be subtracted from the predetermined bolus doses.

In some embodiments, the user can accept a selected bolus (304), manually choose the bolus value (306) and/or select an alternative bolus from the bolus grid (309). Irrespective whether the bolus is directly selected with the aim of the bolus selector, or subsequently modified and selected while taking into consideration the administering history, the bolus delivery at the step (310) can be initiated by transmitting a command from the remote control unit and/or by manual input by virtue of bolus buttons, in some embodiments, located on the dispensing patch unit.

A bolus selected from the bolus-grid can also be delivered automatically and tactile, audible or vibrational alerts can be used to notify the patient prior to the bolus delivery, after the bolus delivery or if the delivery is suspended. In one embodiment, the dispensing device can be used for delivery of insulin and it can be configured as a skin adhered pump. In another embodiment, other devices for insulin delivery can be used (e.g. insulin pumps, injection pens, etc.).

Figure 10:
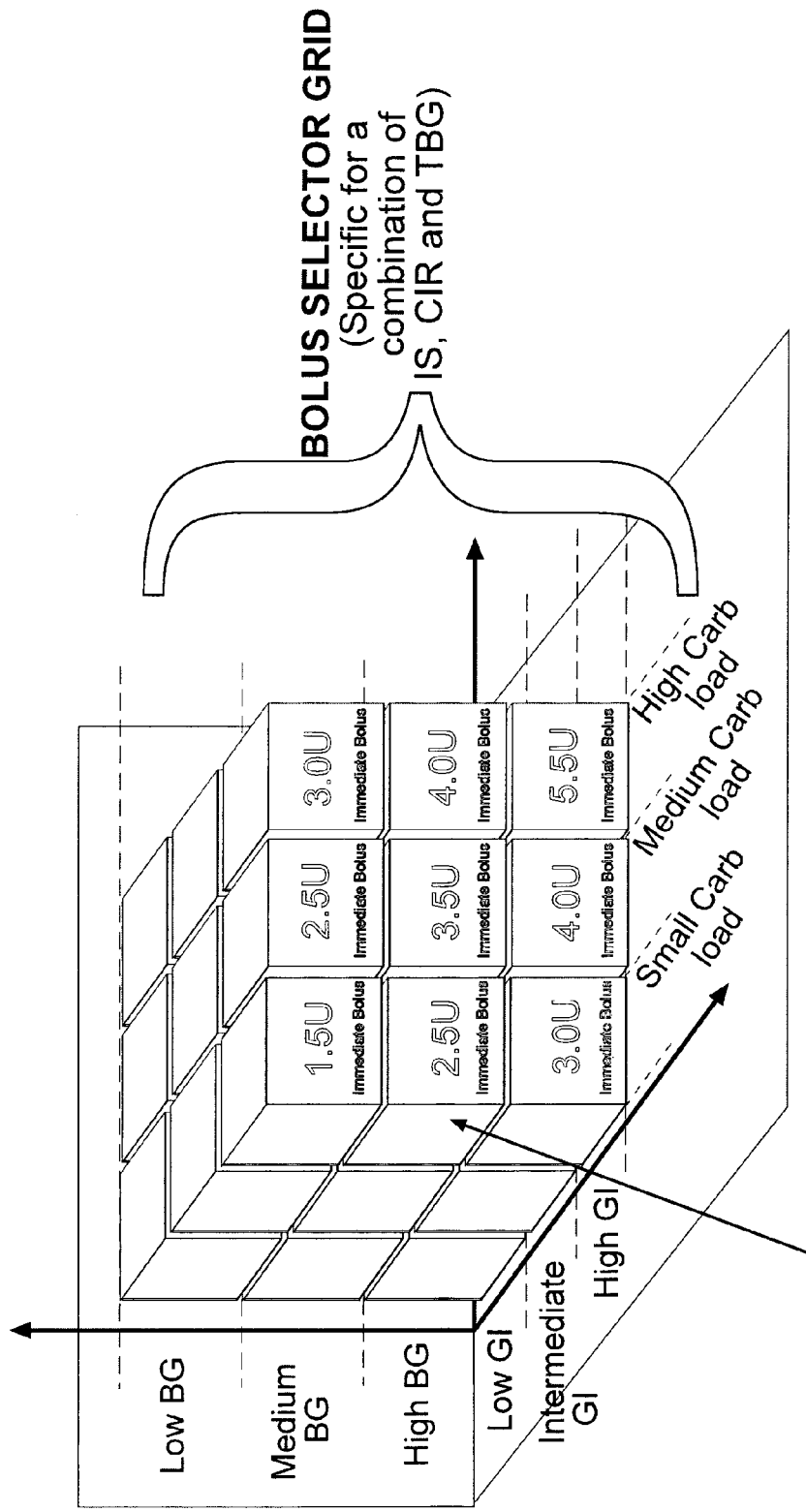
FIG. 10 illustrates an example of a three dimensional bolus-grid with insulin bolus dosages and delivery patterns corresponding to carb load, GI, and current blood glucose levels according to some embodiments of the present disclosure.

FIG. 10 illustrates an embodiment of a three-dimensional bolus-grid with pre-determined insulin bolus dosages and with delivery patterns corresponding to given carb load, GI, and current blood glucose measurements. The 3D grid in the FIG. 10 illustrates a bolus-grid which can be suitable, for example, for a patient with a high carbohydrate-to-insulin ratio (CIR) (e.g. 40 g/unit), high insulin sensitivity (IS) (e.g. 100 mg/dL/unit), and normal gastric emptying and glucose absorption rate.

FIGS. 11a-d provide some examples of "two dimensional" slices of three dimensional bolus-grids with pre-determined insulin bolus dosages and with pre-established delivery patterns corresponding to a given carb load, GI, and current blood glucose measurements. For example, the 2D slice illustrated in the FIG. 11a corresponds to a low GI meal. For example, when a low GI is selected, an extended bolus (e.g. over 6 hours) may need to be delivered. FIG. 11(a) shows a bolus-grid which can be suitable for a patient with a high carbohydrate-to-insulin ratio (CIR) (e.g. 30 g/unit) and with high insulin sensitivity (IS) (e.g. 80 mg/dL/unit).

FIG. 11(b) illustrates a bolus-grid which can be suitable for a patient with an average carbohydrate-to-insulin ratio (e.g. 15 g/Unit.) and with average insulin sensitivity (e.g. 40 mg/dL/unit), for example. FIG. 11(c) illustrates a bolus-grid which can be suitable for a patient with a low carbohydrate-to-insulin ratio (e.g. 7.5 g/unit) and with low insulin sensitivity (e.g. 20 mg/dL/unit). FIG. 11(d) illustrates a bolus grid which can be suitable for a patient with an average carbohydrate-to-insulin ratio (e.g. 15 g/unit.), an average insulin sensitivity (e.g. 40 mg/dL/unit), and with slow gastric emptying (e.g. diabetes induced gastroparesis).

Figure 12:
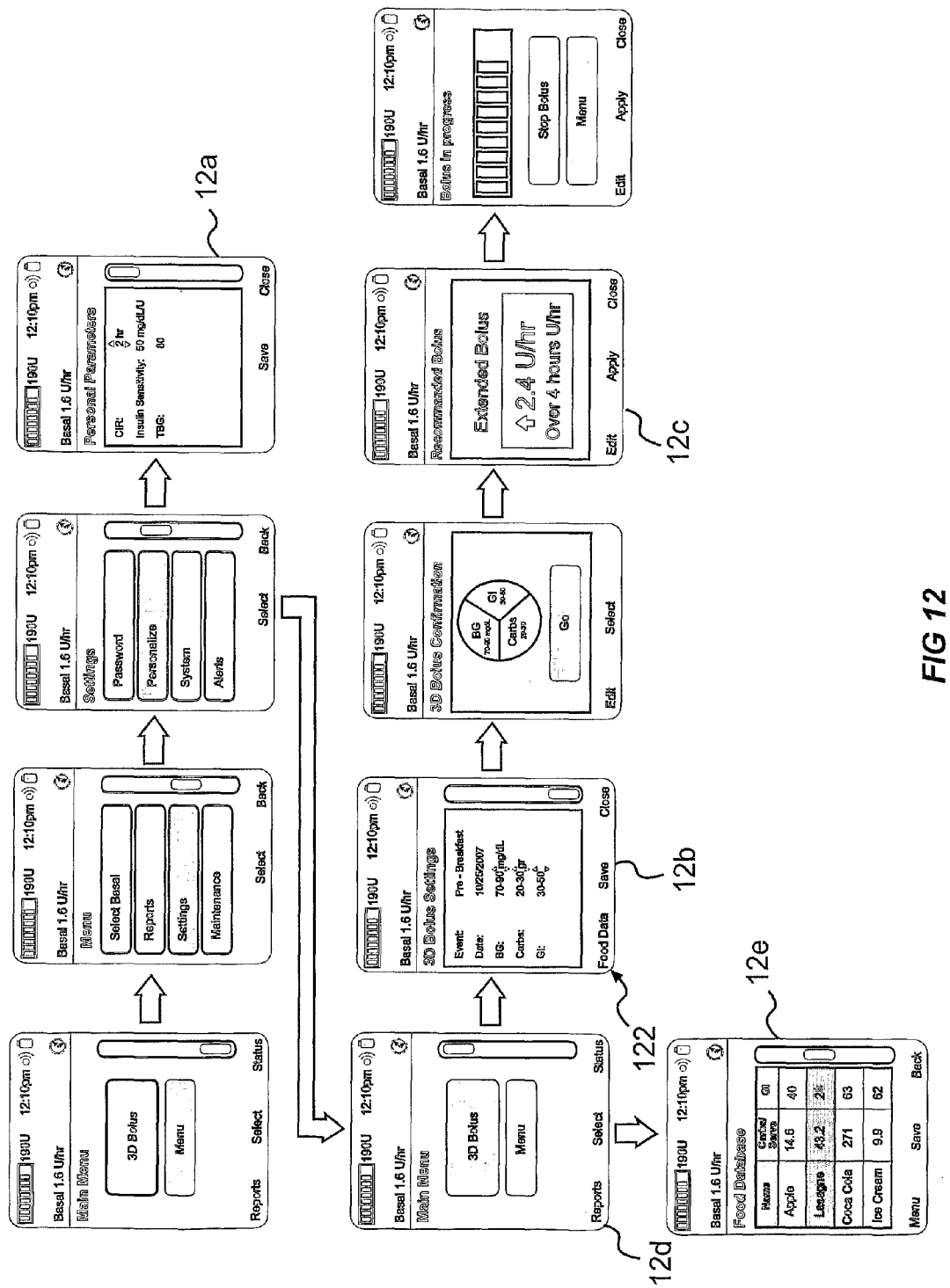
FIG. 12 provides one example of a bolus selector user interface, including a series of window/display flow, according to some embodiments of the present disclosure.

With continuous reference to FIG. 7, FIGS. 12-15 illustrate various embodiments of configuration of the interface (2040) displayed by the bolus selector (2000). FIG. 12 illustrates one example of a user interface for the bolus selector (2000) having navigation windows for the data input. 12a illustrates an example of a window for setting the carbohydrate-to-insulin ratio (CIR), insulin sensitivity (IS), and target blood glucose (TBG) parameters. According to some embodiments, the user can also set the rules for obtaining the IS value and the CIR. 12b provides an example of a window for setting current blood glucose levels, carbohydrate load of the intake, and GI of the intake parameters. If a meal comprises more than one GI (for example a pizza and a cake for dessert), a "combined GI" can also be selected. The bolus selector may comprise delivery patterns suitable for meals containing combined glycemic indexes, for example, high GI+Low GI or high GI+intermediate GI.

The user may enter into a database associated with various food via the window depicted in 12b by pressing the "Food Data" soft key (122). 12c illustrates an example of a window, displaying a recommended selected bolus (bolus dose and delivery pattern). 12d illustrates an example of a main window of the bolus selector (2000) through which the user can select any of the windows presented in 12a-c. Additional windows can be accessible via the main window (e.g. a window for downloading recent bolus data). 12e illustrates an example of a window, displaying a database with the carb load and GI associated with different foods and beverages.

Figure 13A:
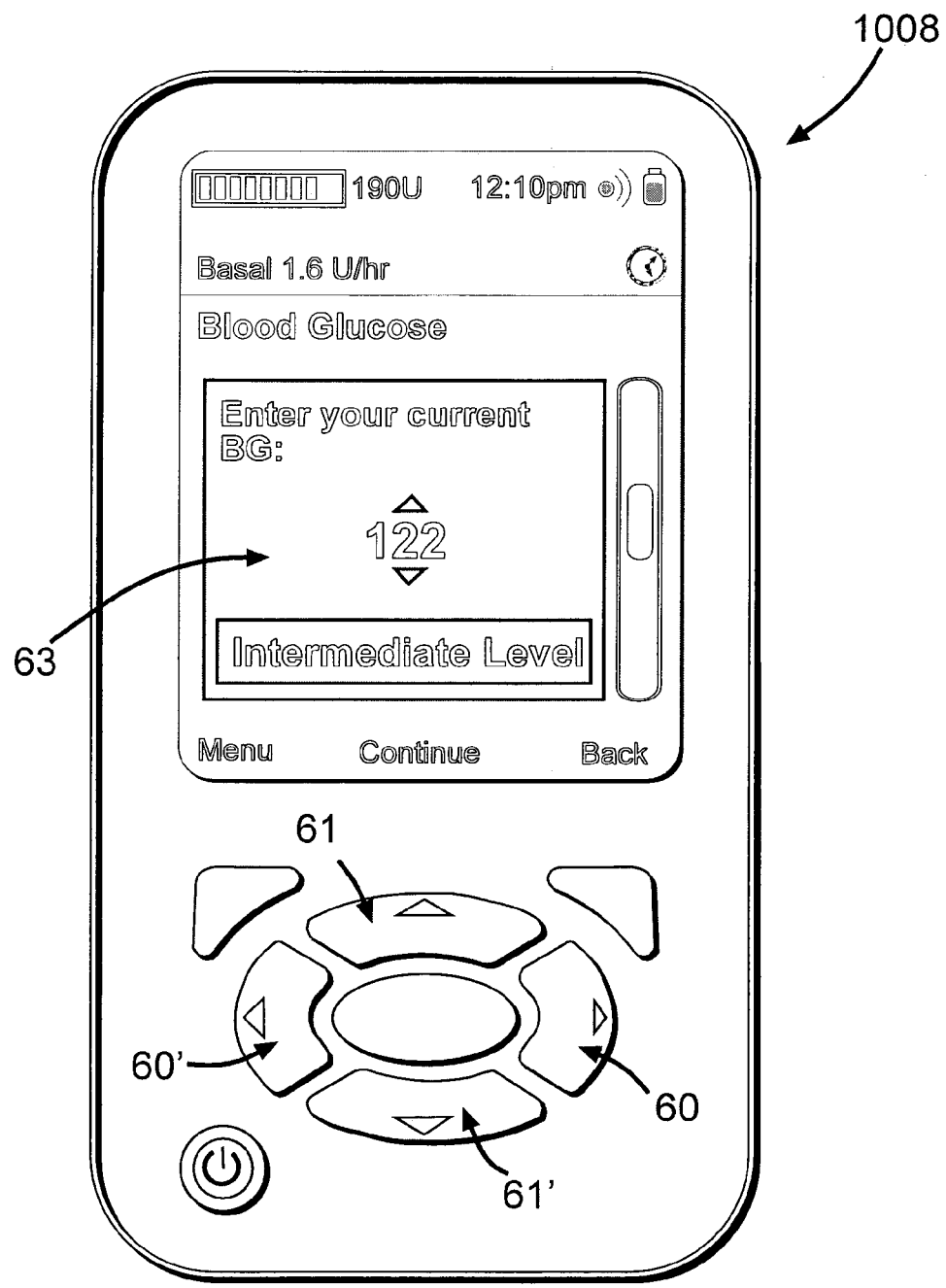
FIGS. 13a-b provide another example of a bolus selector user interface, including, for example, the windows shown in the figures, where the carb load of the intake and the GI of the intake are used for selecting the bolus, according to some embodiments of the present disclosure.
Figure 13B:
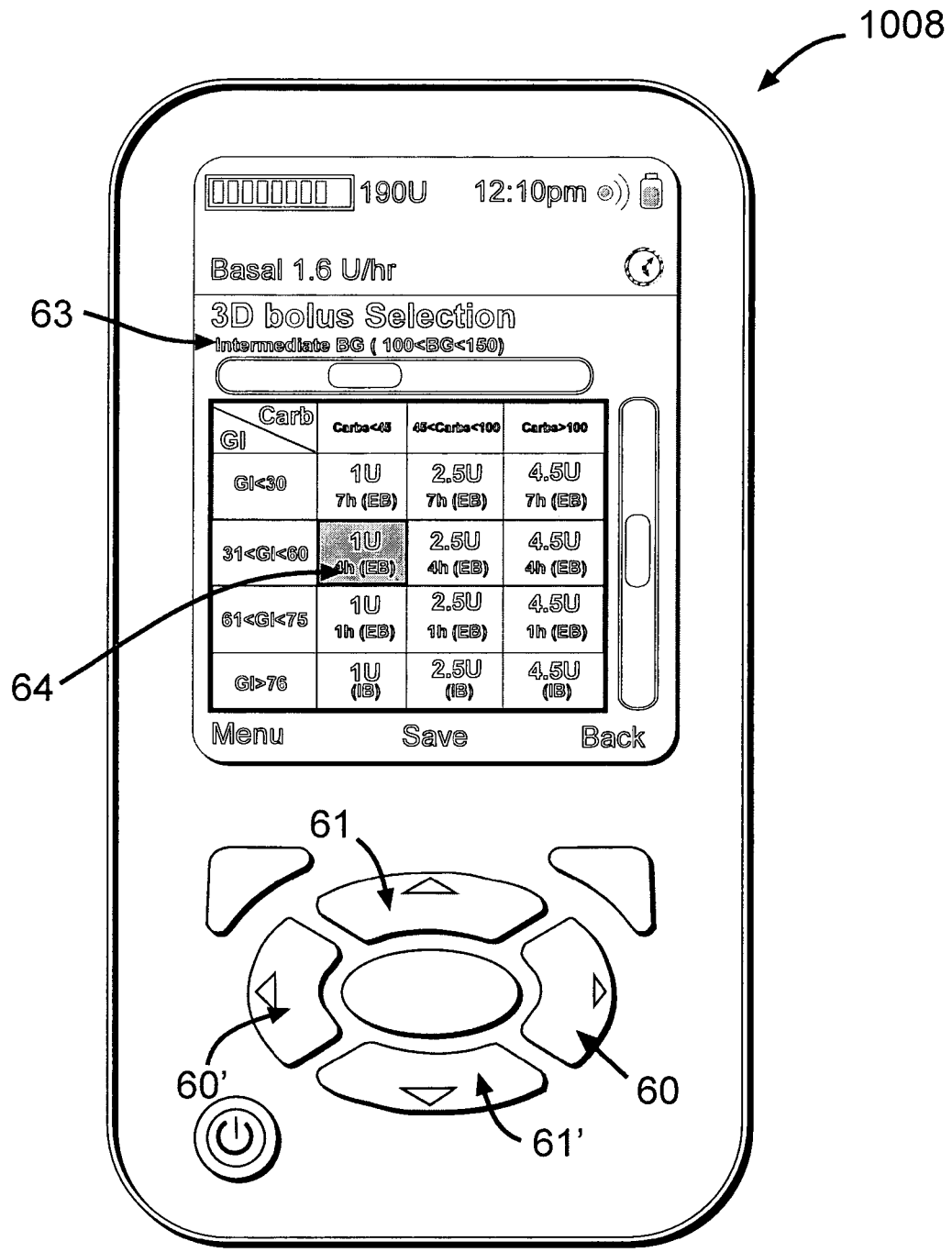

FIGS. 13a-b show an embodiment of the user interface for the bolus selector (2000) in which the user can enter his/her BG value (FIG. 13a). In this embodiment merely a 2 dimensional slice of the 3D bolus grid that corresponds to the entered BG range is displayed (FIG. 13b). In some embodiments, the user can select the required bolus by scrolling the buttons (60,60',61,61') and navigating between different numerical ranges. These ranges quantitatively represent the carb load of the intake and the GI of the intake, accordingly. The recommended bolus dose and delivery pattern can be indicated, as shown by numeral 64. The possible bolus delivery pattern in the example is one of the following: immediate bolus (IB), extended bolus (EB) over 1, 4, or 7 hours. Blood glucose value input (63) (e.g. BG=122) can be ascribed by the bolus selector (2000) to the relevant range of BG values (e.g. 100<BG<150).

Figure 14:
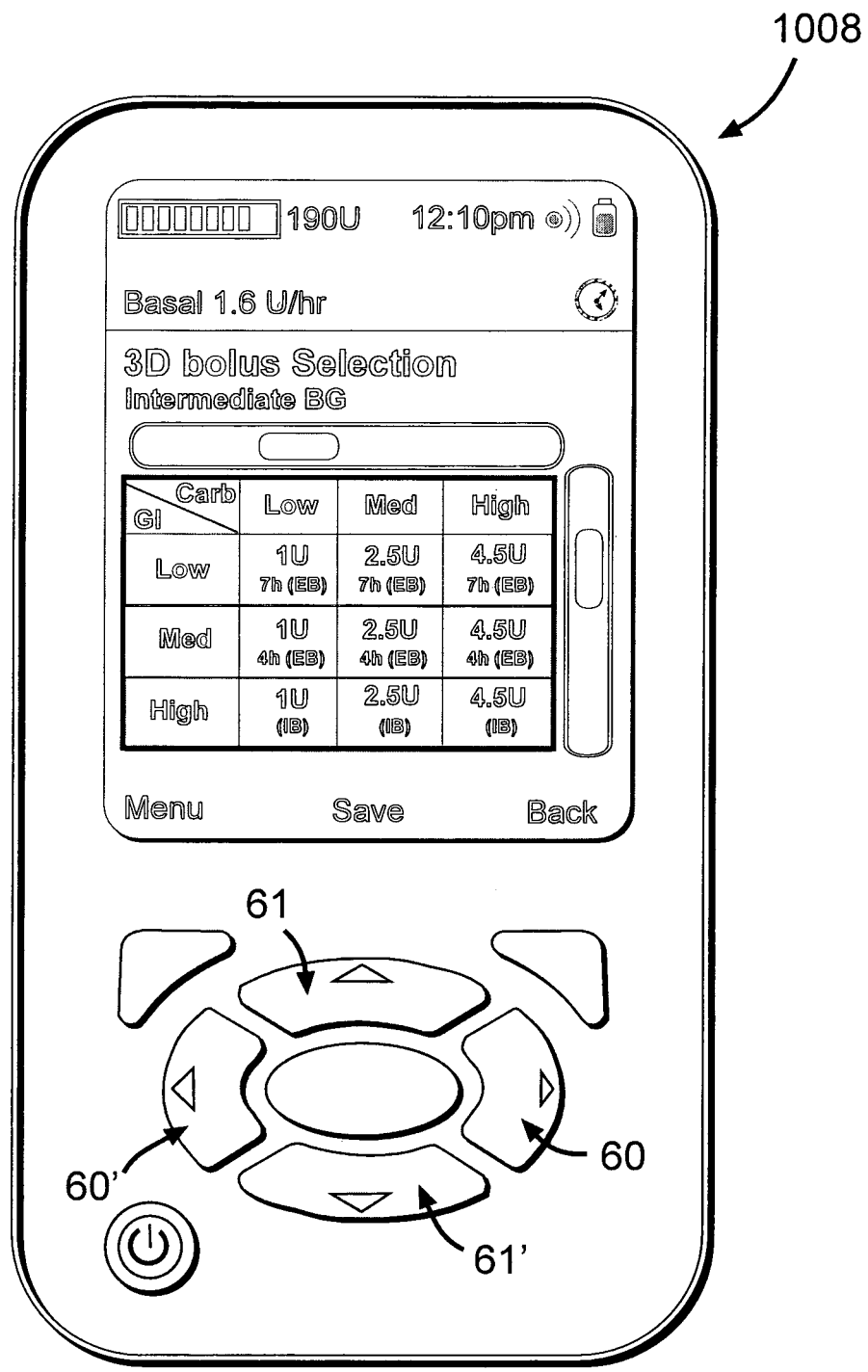
FIG. 14 illustrates another example of a bolus selector user interface, where the carb load of the intake and the GI of the intake are used for selecting the bolus, for example, according to some embodiments of the disclosure.

FIG. 14 illustrates another embodiment of the user interface for the bolus selector (2000) in which a 2 dimensional slice of the 3D bolus grid that corresponds to the relevant BG range is displayed. In such an embodiment, the user can select the required bolus by scrolling the buttons (61, 61', 60, 60') and navigating between different options qualitatively (for example). For example, the options can represent the GI of the intake and the carb load of the intake. The blood glucose value input (63) (e.g. BG=122), as shown in FIG. 13a, can be ascribed by the bolus selector (2000) to the relevant range of BG values (e.g. "Intermediate BG").

Figure 15:
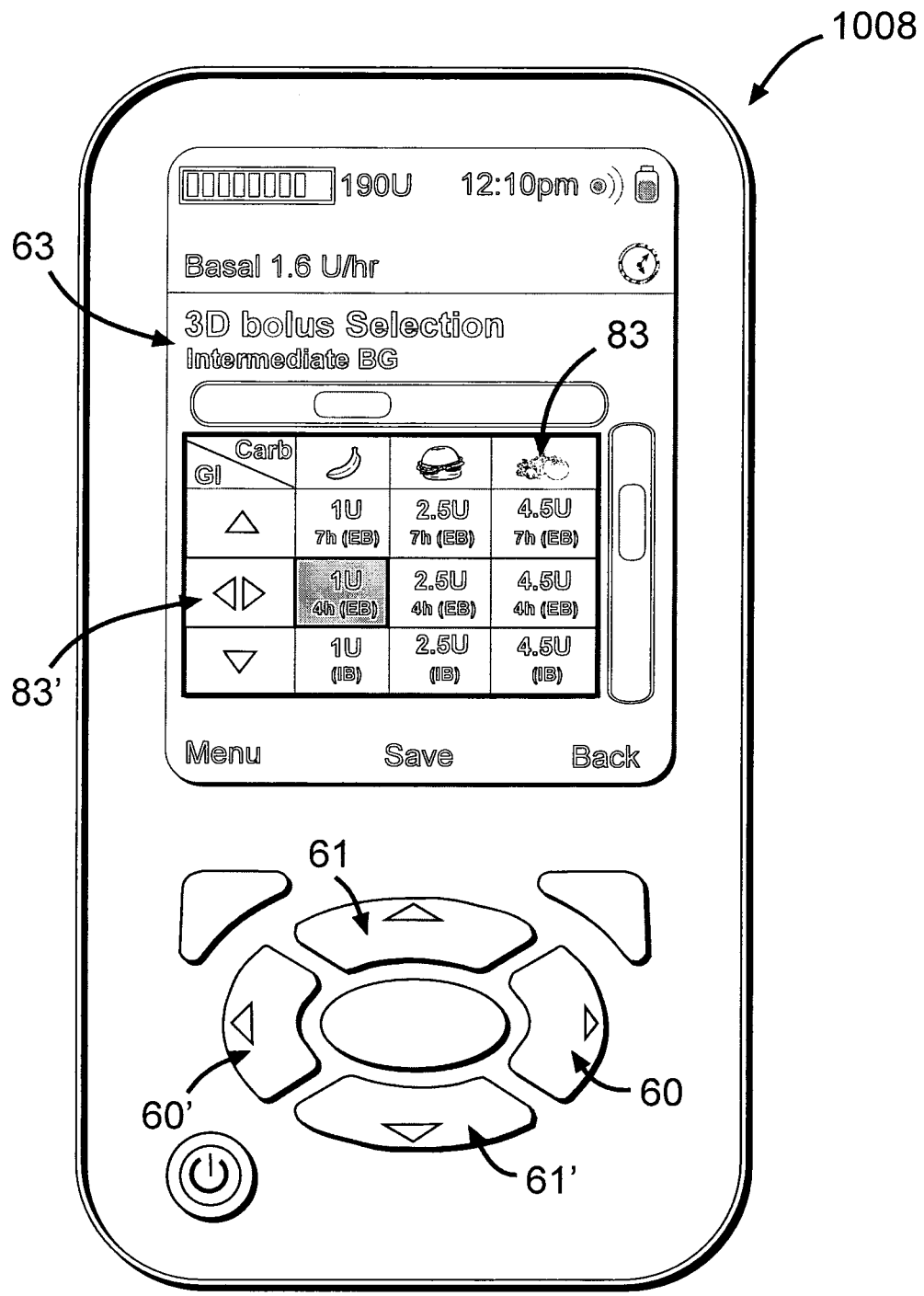
FIG. 15 illustrates a still further example of the bolus selector user interface where the carb load of the intake and the GI of the intake are used for selecting the bolus, according to some embodiments of the disclosure.

FIG. 15 illustrates another embodiment of the user interface for the bolus selector (2000) in which a 2 dimensional slice of the 3D bolus grid that corresponds to the relevant BG range is displayed. According to this implementation, the user can select the required bolus by scrolling the buttons (61',61, 60,60') and navigating between different options (83', 83) represented graphically as an animation associated with the GI of the intake and the carb load of the intake. In one variation, the blood glucose value input (63) (e.g. BG=122), as shown in FIG. 13a, can be ascribed by the bolus selector (2000) to the relevant range of BG values (≤BG). Young children and illiterate users can especially benefit from the graphical user interface illustrated in FIG. 15.

Figure 16A:
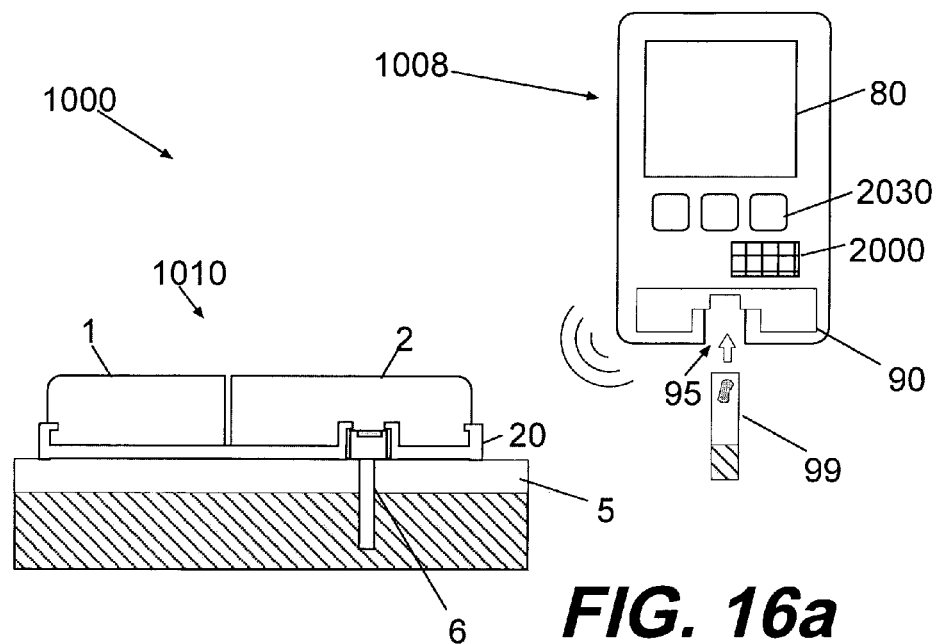
Figure 16B:
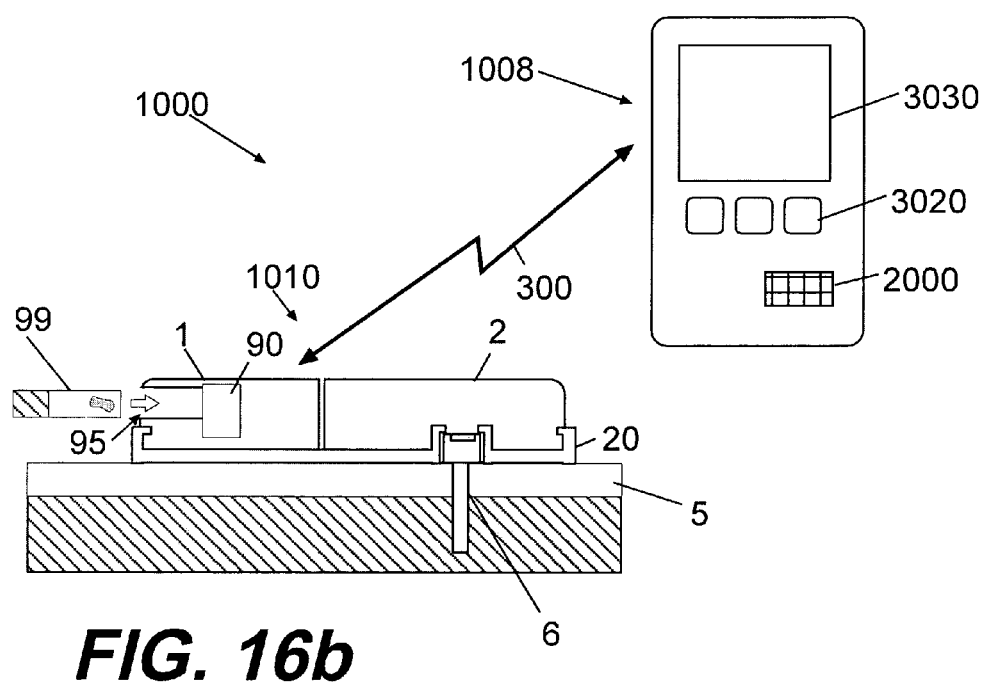

FIGS. 16a-16c show three different embodiments of the device, each containing a glucometer (90) to be used for measuring and inputting the blood glucose (BG) inputs for the bolus selector (2000). FIG. 16a illustrates a glucometer (90) located in the remote control unit (1008) of the drug delivery device. The glucometer (90) comprises an opening (95) for receiving of a test strip (99). A user can extract blood from the body, place the blood on the test strip (99) and inserts the strip into the opening (95). The glucose readings can be displayed on the screen (80) of the remote control unit (1008).

FIG. 16b illustrates a glucometer (90) located in the reusable part (1) of the dispensing patch unit (1010). A communication channel (300) between the glucometer (90) residing in the dispensing patch unit (1010) and the bolus selector (2000) residing in the remote control unit (1008) is maintained, allowing programming, data handling, and user inputs. FIG. 16c illustrates an embodiment in which glucose readings can be received from a separate independent glucometer (90).

Figure 17B:
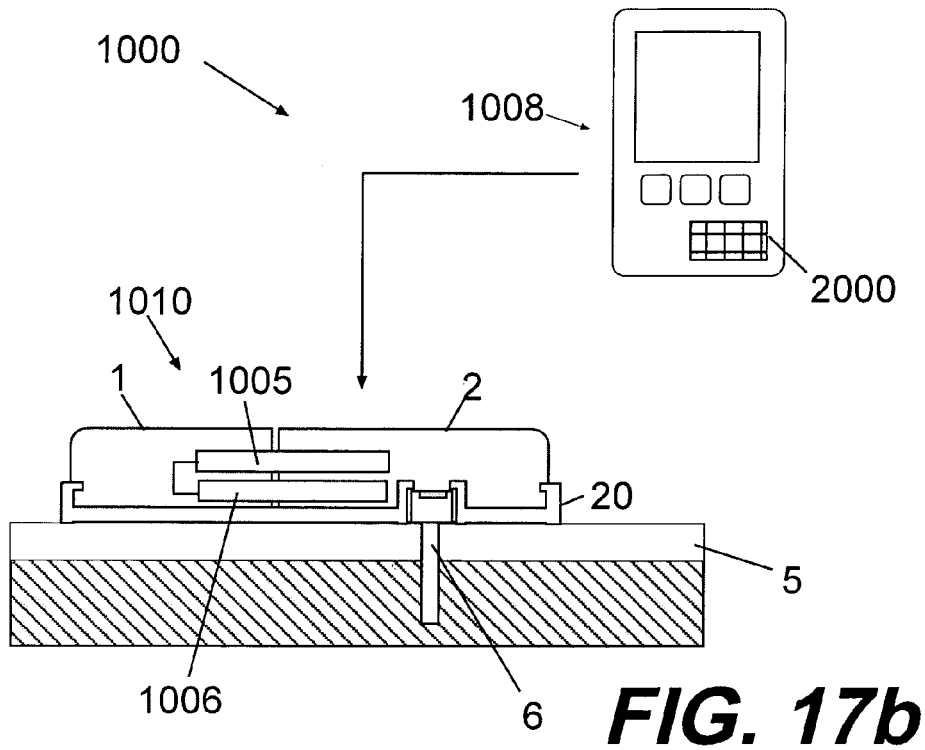

FIGS. 17a-b show another embodiment of the disclosure in which blood glucose readings can be manually loaded to the bolus selector (2000), or automatically received by the bolus selector (2000), from a continuous subcutaneous glucose monitor (1006). A communication channel between the continuous subcutaneous glucose monitor (1006) and the bolus selector (2000) residing in the remote control unit (1008) can be maintained, allowing programming, data handling, and user inputs.

FIG. 17a illustrates an embodiment in which the current blood glucose concentration is received from an independent continuous subcutaneous glucose monitor (1006) and loaded by the patient to the bolus selector (2000). FIG. 17b illustrates an embodiment in which the continuous subcutaneous glucose sensing apparatus (1006) is located in the dispensing patch unit (1010) of the insulin delivery device.

As disclosed in our previous PCT application PCT/IL07/000163, herein incorporated by reference in its entirety, the insulin dispensing apparatus (1005) and glucose sensing apparatus (1006) constitute, in the illustrated embodiment, a single insulin delivery device, and may share a single cannula (6) for both dispensing and sensing functions. Alternatively, the sensing apparatus and the dispensing apparatus may have separate cannulae that penetrate the skin (5) and reside in the subcutaneous tissue.

In another embodiment, the device can be configured to operate as a semi-closed loop system. In a semi-closed system, the feedback and control between sensor measurements and therapeutic fluid release can be partially automatic. For example, the release of the therapeutic fluid in a basal rate can be automatically controlled by the processor based on various measurements of analytes, while the release of bolus doses of the therapeutic fluid can still be delivered based on according to the user's input. Insulin can automatically be dispensed according to continuous monitoring of glucose levels and according to additional user inputs (semi-closed loop). For example, the bolus selector (2000) can be used for bolus inputs in the semi-closed loop system.

Figure 18:
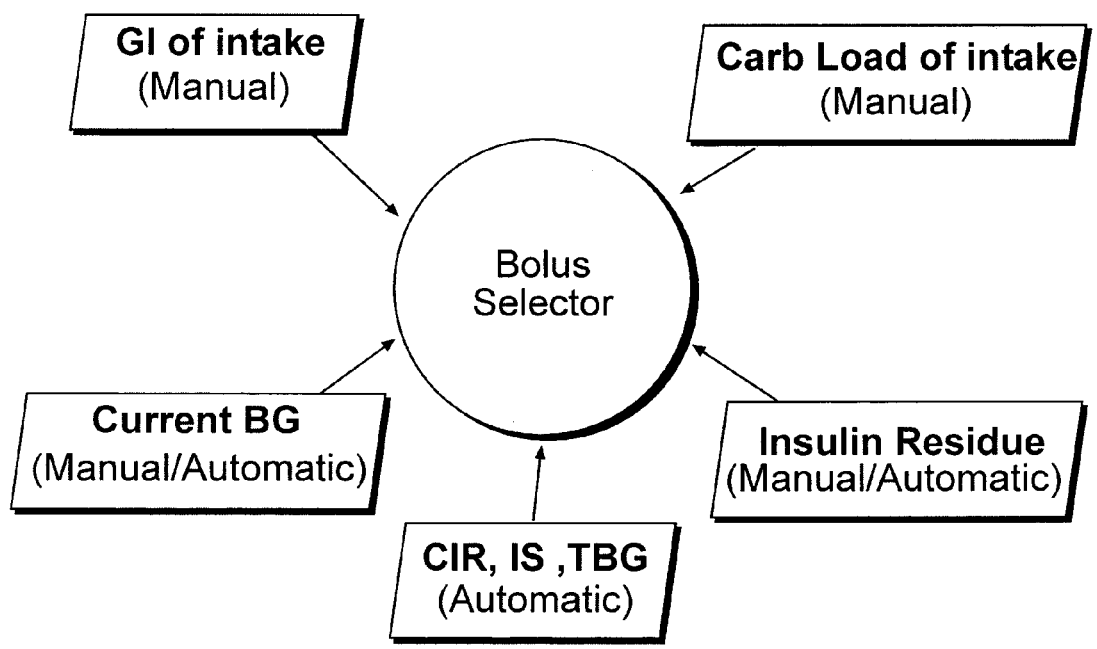
FIG. 18 is a block diagram illustrating data acquisition modes that, in some embodiments, can be used by the bolus selector.

FIG. 18 illustrates the bolus selector data inputs that can be used for patient specific bolus-grid retrieval by the bolus selector (2000). The carbs load of the intake and GI of the intake can be manually configured. The current blood glucose levels can also be manually configured. For example, the user can check his blood glucose level with the aid of a glucometer, a continuous subcutaneous glucose monitoring device, or any other suitable means known in the art for measuring blood glucose levels.

Alternatively, the current blood glucose levels can be configured automatically. For example, the device can comprise a glucometer and a communication channel between the bolus selector and the glucometer, to allow direct input of the measured blood glucose levels. In another embodiment, a communication channel can exit between the bolus selector and an independent glucometer, to allow direct input of the measured blood glucose levels.

In another embodiment, a continuous subcutaneous glucose monitoring apparatus can continuously transmit BG levels to the bolus selector. According to another embodiment, a communication channel can exist between the bolus selector and an independent continuous subcutaneous glucose monitoring device, allowing direct transmission of the measured blood glucose.

The data concerning the residual insulin (time and dose of last bolus) can be obtained manually or automatically, allowing subtraction of the appropriate amount from the selected bolus dose. The carbohydrate-to-insulin ratio (CIR), insulin sensitivity (IS), and target blood glucose (TBG) can be used by the bolus selector according to the initial settings of the user. In some embodiments, the CIR, IS and TBG values can be adjusted manually.

Figure 19:
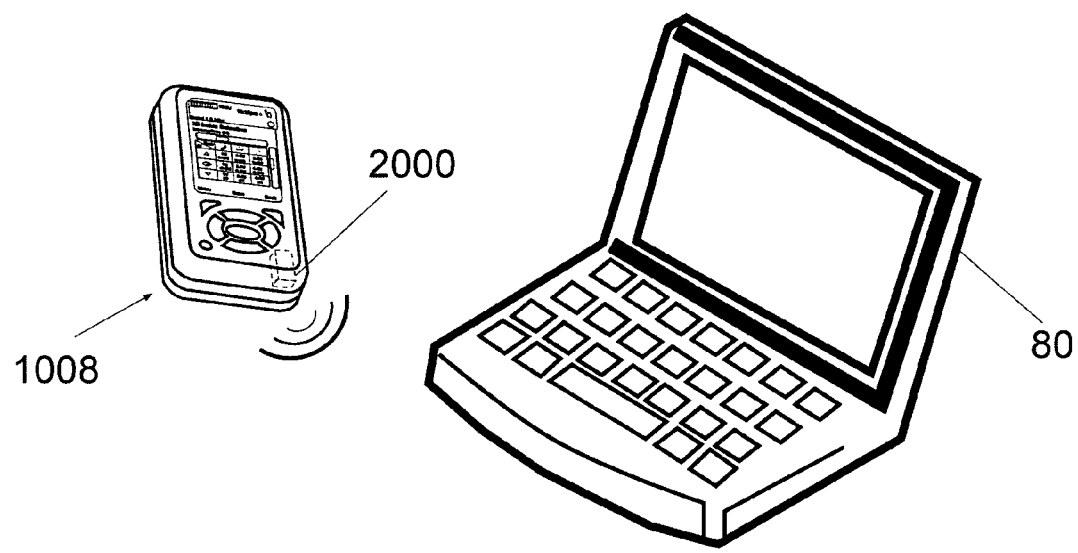
FIG. 19 illustrates another embodiment of the bolus selector that can be located in a remote control unit and/or PC, according to some embodiments of the present disclosure.

FIG. 19 illustrates another embodiment of the device, where the bolus selector (2000), is located in a remote control unit (1008) and communicates with an external PC (80). In some embodiments, the 3D bolus-grids that correspond to the user's particular preset IS value, CIR, and TBG may be saved in the memory of the bolus selector (2000) in the remote control (1008) while the rest of the bolus-grids (i.e. bolus-grids that correspond to other IS values, CIR Ratios, or TBG values) can be saved in the memory of the external PC (80). If the diabetic state of the user changes, the bolus-grids that correspond to, the new IS and/or CIR and/or TBG can be downloaded from the external PC (80) to the bolus selector memory in addition to, or instead of, the previous stored 3D bolus-grids.

According to some embodiments, the delivery patterns of the bolus-grids can be tailored to a specific user. Different users may require different delivery patterns for the same GI. For example, a user with gastroparesis may require delivery patterns over longer periods of time to accommodate for the slow gastric emptying. On the other hand, users who suffer from dumping syndrome may need delivery patterns over shorter periods of time to accommodate for the rapid gastric emptying.

The tailoring of the bolus-grids, prior to the system use, can be carried out directly via the remote control unit (1008), for example. The bolus-grids can also be pre-determined with the aim of a PC (80) and downloaded afterwards to the bolus selector (2000) residing in the remote control unit (1008).

FIG. 20a illustrates an example of a 2 dimensional slice of the 3D bolus grid, corresponding to an intake with a high GI. In this case, an immediate bolus can be recommended. The bolus-grid in the example can be suitable for a user with an IS value of 40 mg/dL/unit, an IS/CIR ratio of 3 (i.e. CIR=13.3 g/unit), and a target BG level of 100 mg/dL. As shown, each range (either of blood glucose (BG) levels or carbs) has a low boundary and a high boundary defining the range, for example. Each range is represented by a discrete value designated as a reference value ("Ref.") which is applied in the calculations of the pre-determined bolus.

In some embodiments, the reference value is not necessarily the mid-range value but rather a value closer to the lower portion of each range. In some embodiments, the reference value may be intentionally shifted during generation of the pre-determined bolus-grids, for example, higher than the mid-range value. In some examples, the reference value may be equal to the upper boundary value (e.g. in a range of 20 to 40, the reference value may be 40). The rationale for this shift is that it may minimize human error in estimating the carb load to be ingested. This error can be frequently caused by the tendency of users to underestimate the amount of carbohydrates.

In some embodiments, during generation of the pre-determined bolus-grids, each cell value of a bolus-grid (presented in units of insulin) can be selected to lead the BG concentrations to fall within a pre-defined allowable clinical range of blood glucose levels, for example. This clinical range can be bounded between two discrete values of blood glucose levels: a lower boundary referred-to as the "minimal undershoot", and an upper boundary referred-to as the "maximal overshoot". The minimal undershoot and the maximal overshoot can be, for example, 60 mg/dL and 200 mg/dL, respectively. If an insulin value within a cell causes the blood glucose level of the patient to be outside of the allowable range, (i.e. <60 mg/dL or >200 mg/dL), the patient can likely suffer from hypoglycemia or hyperglycemia, which may be hazardous.

According to some embodiments, the selection of a value of insulin bolus dose for a particular cell can be done using a verification process that tests the boundary values of the blood glucose range and the carbohydrate intake range corresponding to that cell.

For example, the cell value which corresponds to the blood glucose (BG) range 130 mg/dL to 160 mg/dL, and carbohydrate intake range of 40 grams to 60 grams can first be calculated according to the reference values, i.e. BG of 145 mg/dL and carbohydrate intake of 45 grams yielding the value of 4.5 units of insulin to be administered. The verification process can calculate a lower value based on the low boundary of the BG and carbohydrate intake ranges (i.e. BG=130 mg/dL and carbs=40 grams), and an upper value based on the high boundary of the ranges (i.e. BG=160 mg/dL and carbs=60 grams), resulting in a lower value of 3.76 Units and the upper value of 6 Units. The absolute difference between the lower value (3.76 Units) and the cell value (4.5 Units) equals to 0.74 Units, and is referred-to as "low_diff". The low_diff difference can bring the BG level of the patient to approximately 70 mg/dL. For example, this can be calculated by using the following formula: TBG−low_diff*IS. Following the example presented above, the low_diff value can bring the BG level of the patient to 100−0.74*40=70.4 mg/dL.

A similar procedure can be done with the upper value: the absolute difference between the upper value (6 Units) and the cell value (4.5 Units) is determined to be 1.5 Units, and referred-to as "upper_diff" (for example). This difference could bring the BG level of the patient to a value of approximately 160 mg/dL. If one of the values (70 mg/dL or 160 mg/dL) falls outside of the clinical range defined by the minimal undershoot and the maximal overshot, then, in some embodiments, the reference value and/or values of the BG and carbohydrate intake ranges can be re-assessed.

The verification procedure described above can be carried out iteratively to determine the optimal cell value ensuring that the BG level of the patient remains in the allowed clinical range. In some embodiments, a single clinical range (i.e. minimal undershoot and maximal overshoot) can be defined for all the cells of the bolus-grid. In some embodiments, a different clinical range can be defined for each cell of the bolus-grid. In some embodiments, the patient/user can define/program parameters such as minimal undershoot, maximal overshoot and/or boundaries of the ranges, adjusting the bolus-grid to be tailored to his/her own individual needs. In some embodiments, the BG levels corresponding to "low_diff" and "upper_diff" values can be pre-calculated and stored in a database table. For example, FIGS. 20b and 20c show the corresponding minimal undershoot and maximal overshoot tables, respectively. Specifically, the table 20b provides a list of minimal undershoot values for each of the BG ranges and for each of the six carbohydrate intake ranges presented in FIG. 20a. In some embodiments, the tables 18b and 18c are not presented to the user.

For example, according to the table 20b, the minimal allowable undershoot value is 70 mg/dL. According to table 20c, the maximum allowable overshoot value is 160 mg/dL. In some embodiments, the undershoot and/or overshoot values, lower and/or upper boundaries of the ranges and other bolus-grid parameters can be adjusted.

Figure 21A:
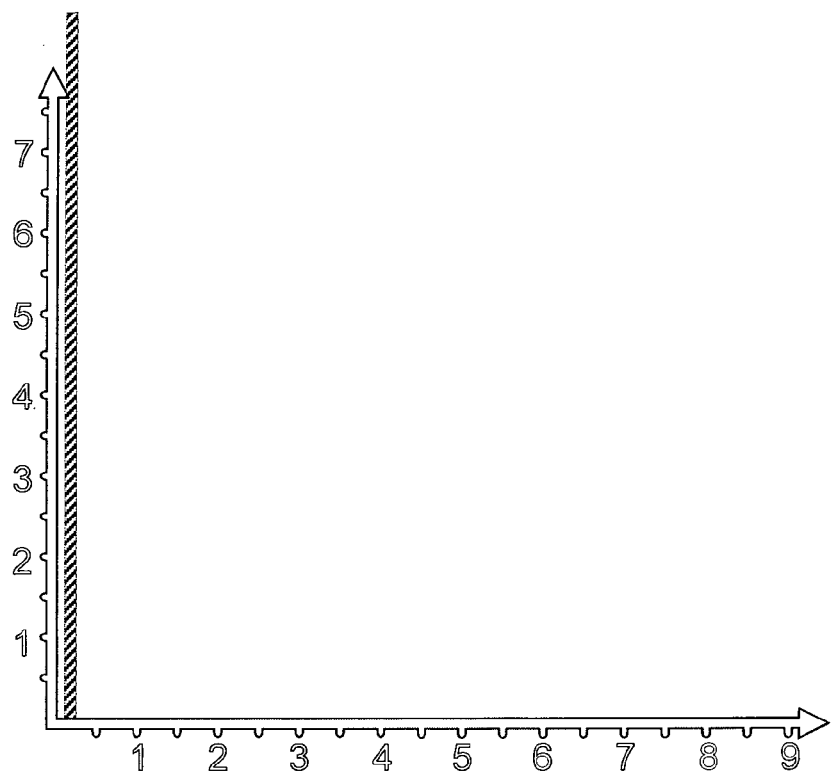
FIG. 21 illustrates examples of a plurality of bolus delivery patterns that can be recommended to the user by the bolus selector according to some embodiments of the present disclosure.

FIGS. 21a-f illustrate graphic representations of exemplary pre-determined bolus delivery patterns which can be recommended to the user by the bolus selector. For example, FIG. 21a depicts a delivery pattern in which the entire bolus dose is delivered as rapidly as possible. This pattern can be suitable for a meal that is rapidly absorbed from the gut, i.e., a meal that is attributed as having a high glycemic index. An example of such meal is cornflakes or fruit.

Figure 21B:
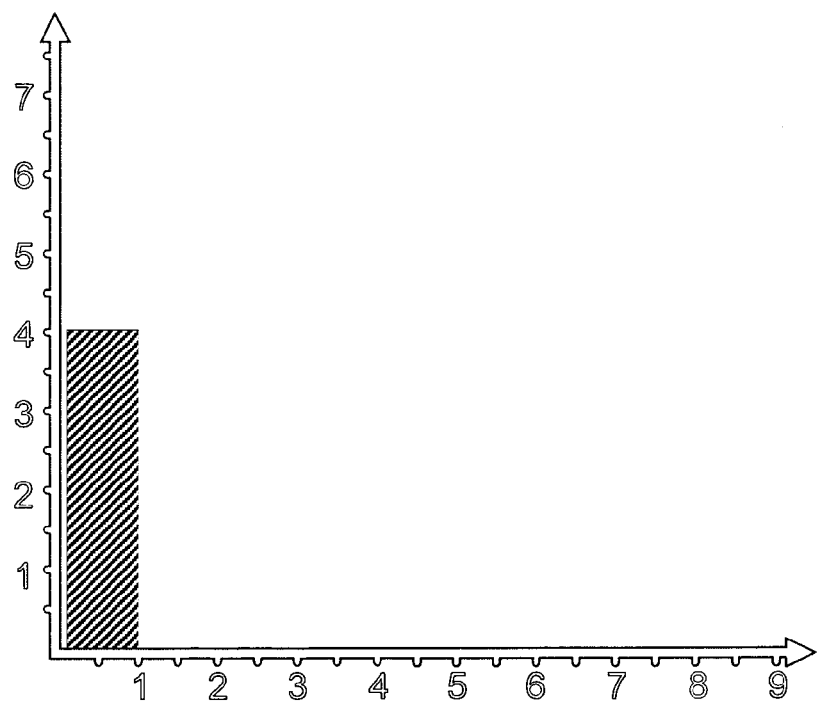
Figure 21C:
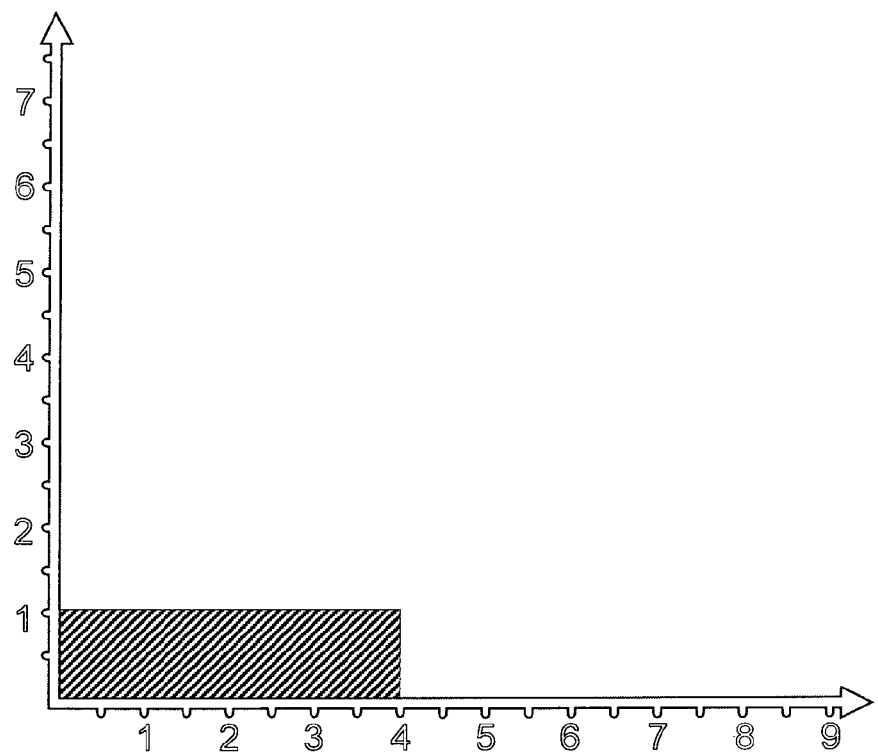

FIG. 21b depicts a delivery pattern in which the bolus dose is delivered evenly over a period of 1 hour. This may be suitable for a meal that is relatively slowly absorbed from the gut, i.e., a meal of a low glycemic index or high in fat, such as pizza. FIG. 21c depicts a delivery pattern in which the bolus dose is delivered evenly over a period of 4 hours. This may be suitable for a meal that is very slowly absorbed from the gut, i.e., a meal of a very low glycemic index or very high in fat, such as steak.

Figure 21D:
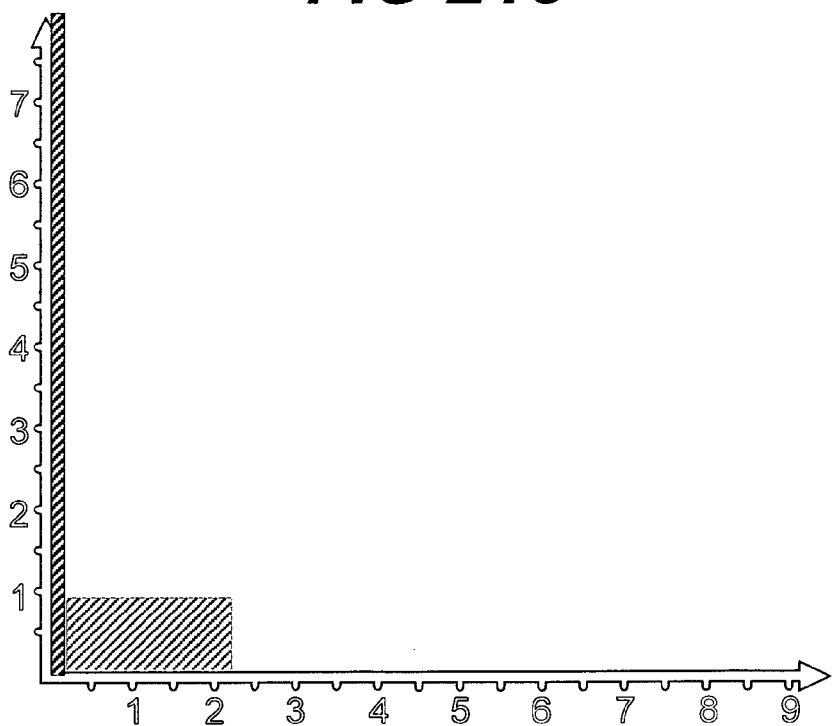

FIG. 21d depicts a delivery pattern in which a portion of the bolus dose is delivered immediately and the remaining dose is delivered evenly over a prolonged period of time. In the depicted pattern, the immediate portion comprises 60% of the total dose, and the remaining 40%. The remaining portion is delivered over the period of 2 hours. For example, such a delivery pattern can be suitable for a meal that comprises both rapidly (high GI) and slowly (intermediate GI) absorbed carbohydrates, such as fruit and pasta.

The pattern depicted on FIG. 21d can also be suitable when the elevated blood glucose value needs to be corrected before a meal corresponding to an intermediate glycemic index. The insulin needed for correction of the BG can be accounted for in the immediate portion of the bolus and the slowly absorbed meal can be accounted for in the proceeding, relatively long, time interval. For example, if a user is planning to eat a meal corresponding to an intermediate GI and the user's current BG is high, then the following two boluses can be used:

an immediate correction bolus delivered to bring the high BG level to a target value; and an extended bolus delivered over a period of time to balance the meal with an intermediate GI.

Figure 21E:
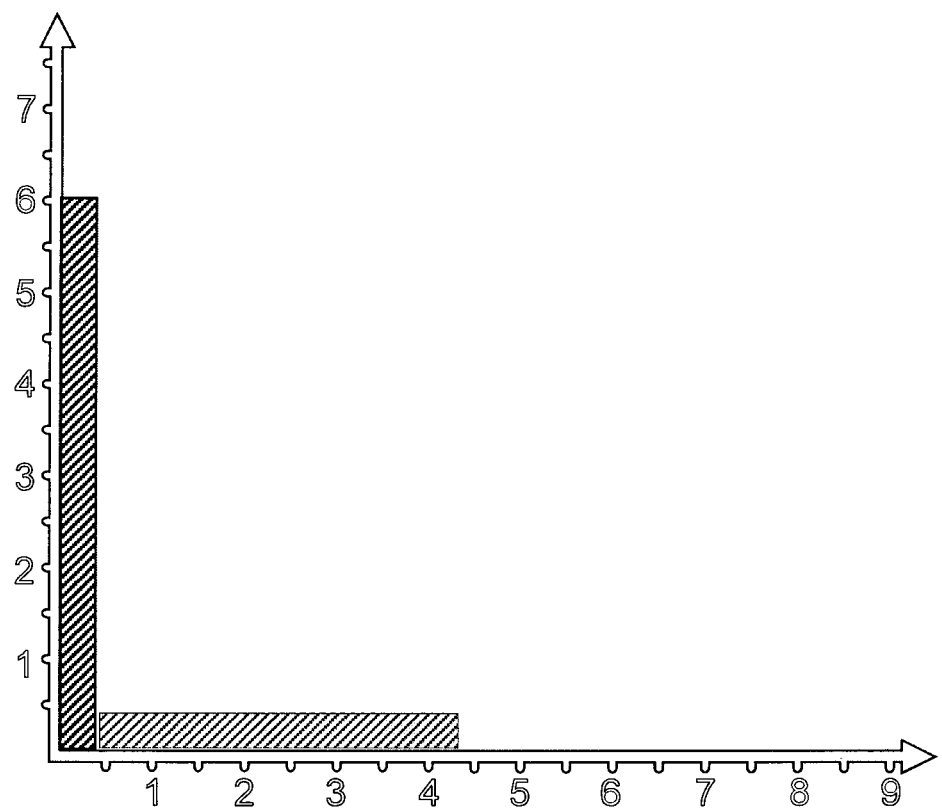

FIG. 21e depicts another delivery pattern in which a portion of the bolus dose is delivered immediately and the remaining dose is delivered evenly over a prolonged period of time. In the depicted pattern, the immediate portion comprises 60% of the total dose, and the remaining 40% are delivered over the following 4 hours. Such a delivery pattern may be suitable for a meal that comprises both rapidly (high GI) and very slowly (low GI) absorbed carbohydrates, such as fruit and pork ribs. Such a pattern is also suitable when correction of elevated blood glucose value is needed before a meal having low glycemic index.

Various embodiments of the subject matter described herein can be realized in digital electronic circuitry, integrated circuitry, specially designed ASICs (application specific integrated circuits), computer hardware, firmware, software, and/or combinations thereof. These various embodiments may include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the term "machine-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the subject matter described herein can be implemented on a computer having a display device (e.g., a CRT (cathode ray tube) or LCD (liquid crystal display) monitor, or other display device) for displaying information to the user and a keyboard and a pointing device (e.g., a mouse or a trackball) by which the user may provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The subject matter described herein can be implemented in a computing system that includes a back-end component (e.g., as a data server), or that includes a middleware component (e.g., an application server), or that includes a front-end component (e.g., a client computer having a graphical user interface or a Web browser through which a user may interact with an implementation of the subject matter described herein), or any combination of such back-end, middleware, or front-end components. The components of the system can be interconnected by any form or medium of digital data communication (e.g., a communication network). Examples of communication networks include a local area network ("LAN"), a wide area network ("WAN"), and the Internet.

The computing system may include clients and servers. A client and server are generally remote from each other and typically interact through a communication network. The relationship of client and server arises by virtue of computer programs running on the respective computers and having a client-server relationship to each other.

Some embodiments of the present disclosure preferably implement the bolus selection feature via software operated on a processor contained in a remote control device of an insulin dispensing system and/or a processor contained in a insulin dispensing device being party of an insulin dispensing system.

Any and all references to publications or other documents, including but not limited to, patents, patent applications, articles, webpages, books, etc., presented in the present application, are herein incorporated by reference in their entirety.

Although a few variations have been described in detail above, other modifications are possible. For example, the logic flow depicted in the accompanying figures and described herein does not require the particular order shown, or sequential order, to achieve desirable results. Other embodiments can be within the scope of the following claims.

What is claimed is:

1. A method for selecting a bolus configuration in a drug delivery device for infusing a drug into a body of a user, the method comprising:
   providing a fluid delivery system including a processor having instructions operating thereon to enable the system and/or allow the system to perform the steps of:
      receiving a current glucose value of a user;
      receiving a carbohydrate load value of a food intake to be consumed by the user;
      receiving one or more additional inputs; and
      automatically determining a bolus configuration to be delivered to the user, wherein the bolus configuration comprises an amount of a drug to be delivered and a delivery pattern;
      wherein determining the bolus configuration comprises:
         displaying to the user at least one grid of one or more bolus configurations stored in a memory, wherein each bolus configuration corresponds to a different combination of values of three or more inputs including the current glucose value of the user, the carbohydrate load value of the food intake to be consumed by the user and the one or more additional inputs, and wherein the at least one grid comprises three or more dimensions, each of the dimensions corresponding to one of the three or more inputs; and
         retrieving a selected bolus configuration from the stored one or more bolus configurations based on user selection of at least one of the one or more bolus configurations via a user interface for determining the bolus configuration to be delivered to the user.

2. The method of claim 1, wherein determining the bolus configuration comprises:
   determining the amount of drug to be delivered based on the current glucose value and the carbohydrate load; and
   determining the delivery pattern based on at least one of the one or more additional inputs.

3. The method of claim 2, wherein the one or more additional inputs is selected from the group consisting of: the glycemic index (GI) of the intake, the content of the intake, glycemic load (GL) of the intake, fat content of the food intake, fiber content of the food intake, residual insulin (RI), and a physiological parameter of the user.

4. The method of claim 1, wherein the bolus configuration is determined based on previous bolus configurations.

5. The method of claim 1, wherein the value of at least one of the current glucose value of the user, the carbohydrate load of a food intake to be consumed and the one or more additional inputs are represented as qualitative descriptive values.

6. The method of claim 5, wherein each qualitative descriptive value comprises one or more value ranges of an input of the at least one of the current glucose value of the user, the carbohydrate load of a food intake to be consumed by the user and the one or more additional inputs.

7. The method of claim 5, wherein the qualitative descriptive values comprise small, medium and large.

8. The method of claim 1, wherein the amount of the drug to be delivered does not exceed a pre-determined maximal overshoot and/or minimal undershoot criteria.

9. The method of claim 8, wherein the maximal overshoot and/or minimal undershoot criteria are configurable by the user.

10. The method of claim 1, further comprising providing a drug delivery device infusing the drug according to the bolus configuration.

11. The method of claim 1, wherein each grid of the at least one grid is defined by one or more user parameters selected from the group consisting of CIR, IS, TBG and RI.

12. The method of claim 1, further comprising providing a user interface for presenting the at least one grid in a multi-dimensional space presentation corresponding to the three or more dimensions of the at least one grid, wherein each bolus configuration is spatially positioned within the multi-dimensional space in accordance to the different values combination of the three or more inputs.

13. The method of claim 1, further comprising providing a user interface for presenting the at least one grid in a two-dimensional space presentation corresponding to two dimensions of the three or more dimensions of the at least one grid, wherein each bolus configuration is spatially positioned within the dimensional space in accordance to the different values combination of the three or more inputs.

14. The method of claim 1, further comprising providing a user interface implemented in a remote control, a skin-securable patch-pump delivering the drug according to the bolus configuration, and optionally a glucometer providing the current glucose value.

15. The method of claim 1, further comprising providing a continuous glucose monitor (CGM) adopted for providing glucose values.

16. A drug delivery system for infusing a drug into a body of a user, the system comprising:
a processor having instructions operating thereon to enable the system to:
receive a glucose value of a user;
receive a carbohydrate load value of a food intake to be consumed by the user;
receive one or more additional inputs; and
automatically determining a bolus configuration, wherein the bolus configuration comprises an amount of a drug to be delivered and a delivery pattern;
wherein determining the bolus configuration comprises:
displaying to the user at least one grid of one or more bolus configurations stored in a memory, wherein each of the one or more bolus configurations corresponds to a different combination of values of three or more inputs including the current glucose value of the user, the carbohydrate load value of the food intake to be consumed by the user and the one or more additional inputs, and wherein the at least one grid comprises three or more dimensions, each of the dimensions corresponding to one of the three or more inputs; and
retrieving a selected bolus configuration from the stored one or more bolus configurations based on user selection of at least one of the one or more bolus configurations via a user interface for determining the bolus configuration to be delivered to the user: and
a drug delivery device for infusing the drug to the user.

17. A method for selecting a bolus configuration in a drug delivery device for infusing a drug into a body of a user, the method comprising:
providing a fluid delivery system including a processor having instructions operating thereon to enable and/or perform the steps of:
receiving values of three or more inputs;
providing a user interface for presenting one or more bolus configurations as at least one grid in a multi-dimensional space presentation corresponding to three or more dimensions, wherein each of one or more the bolus configurations corresponds to a different combination of three or more input values, and wherein each of the one or more bolus configurations is spatially positioned within the multi-dimensional space in accordance to the different values combination of the three or more inputs; and
retrieving a selected bolus configuration, from the memory, based on user selection of at least one of the bolus configurations via the user interface; the selected bolus configuration comprising an amount of drug to be delivered and a delivery pattern.

18. The method of claim 17, wherein:
the three or more inputs include a current glucose value and carbohydrate load of a food intake to be consumed by the user; and
determining the bolus configuration comprises determining the amount of drug to be delivered based on the current glucose value and the carbohydrate load and determining the delivery pattern based on at least one other input of the three or more inputs.

19. The method of claim 18, wherein at least one other input of the three or more inputs is selected from a group consisting of: a content of the intake, a GI of the intake, a fat content of the intake, a fiber content of the intake, a glycemic load (GL) of the intake, a residual insulin (RI) and one or more physiological parameters of the user.

* * * * *